United States Patent
Robison et al.

(10) Patent No.: US 12,172,011 B2
(45) Date of Patent: Dec. 24, 2024

(54) ADAPTIVE STIMULATION ARRAY FOR MOTOR CONTROL

(71) Applicant: Cionic, Inc., San Francisco, CA (US)

(72) Inventors: Jeremiah Robison, San Francisco, CA (US); Lina Avancini Colucci, Los Altos, CA (US); Ren Gibbons, Oakland, CA (US)

(73) Assignee: Cionic, Inc., San Francisco, CA (US)

( * ) Notice: Subject to any disclaimer, the term of this patent is extended or adjusted under 35 U.S.C. 154(b) by 456 days.

(21) Appl. No.: 17/397,669

(22) Filed: Aug. 9, 2021

(65) Prior Publication Data

US 2023/0039154 A1    Feb. 9, 2023

(51) Int. Cl.
*A61N 1/00*    (2006.01)
*A61B 5/00*    (2006.01)
(Continued)

(52) U.S. Cl.
CPC ........ *A61N 1/36003* (2013.01); *A61B 5/0205* (2013.01); *A61B 5/0533* (2013.01); *A61B 5/1038* (2013.01); *A61B 5/112* (2013.01); *A61B 5/313* (2021.01); *A61B 5/395* (2021.01); *A61B 5/4848* (2013.01); *A61B 5/6804* (2013.01); *A61N 1/0452* (2013.01); *A61N 1/0476* (2013.01); *A61N 1/0484* (2013.01); *A61N 1/36031* (2017.08); *G16H 40/63* (2018.01);
(Continued)

(58) Field of Classification Search
CPC ........................ A61N 1/36003; A61N 1/36031
USPC .......................................................... 607/49
See application file for complete search history.

(56) References Cited

U.S. PATENT DOCUMENTS

| 5,167,229 A | 12/1992 | Peckham et al. |
| 2013/0123568 A1 | 5/2013 | Hamilton et al. |

(Continued)

FOREIGN PATENT DOCUMENTS

WO    WO-2004036370 A2 *   4/2004   ......... A61N 1/36146

OTHER PUBLICATIONS

PCT International Search Report and Written Opinion, PCT Application No. PCT/US2022/38153, Jan. 5, 2023, 13 pages.
(Continued)

*Primary Examiner* — Nicole F Lavert
*Assistant Examiner* — Nicole F Johnson
(74) *Attorney, Agent, or Firm* — Fenwick & West LLP

(57) ABSTRACT

A mobility augmentation system assists a user's movement by determining a corresponding electrical stimulation for the movement. A wearable stimulation array includes sensors, electrodes, an electrode multiplexer, and a controller that executes the mobility augmentation system. The sensors measure movement data, and the mobility augmentation system applies a movement model to the measured movement data. The model can determine different electrical actuation instructions depending on the movement stimulated. For example, to stimulate a knee flexion, the movement model output enables a first set of the electrodes to operate as cathodes and a second set of electrodes to operate as anodes. To stimulate a knee extension, the first set of electrodes can be enabled to operate as anodes and a third set of electrodes as cathodes. The user can provide feedback of the applied stimulation, which the system can use to retrain the model and optimize the stimulation to the user.

20 Claims, 8 Drawing Sheets

(51) Int. Cl.
  *A61B 5/0205* (2006.01)
  *A61B 5/0533* (2021.01)
  *A61B 5/103* (2006.01)
  *A61B 5/11* (2006.01)
  *A61B 5/313* (2021.01)
  *A61B 5/395* (2021.01)
  *A61N 1/04* (2006.01)
  *A61N 1/36* (2006.01)
  *G16H 40/63* (2018.01)
  *G16H 50/20* (2018.01)

(52) U.S. Cl.
  CPC ...... *G16H 50/20* (2018.01); *A61B 2562/0219* (2013.01)

(56) References Cited

U.S. PATENT DOCUMENTS

| | | |
|---|---|---|
| 2016/0303376 A1 | 10/2016 | Dinsmoor et al. |
| 2017/0303849 A1 | 10/2017 | De Sapio et al. |
| 2017/0312515 A1* | 11/2017 | Ferree ................ A61N 1/36021 |
| 2018/0015284 A1 | 1/2018 | Coleman et al. |
| 2018/0036531 A1* | 2/2018 | Schwarz ................ A61B 5/332 |
| 2020/0197689 A1* | 6/2020 | Dernebo ............... A61N 1/3603 |
| 2020/0406035 A1 | 12/2020 | Sharma et al. |
| 2022/0175555 A1 | 6/2022 | Robison et al. |
| 2022/0176545 A1 | 6/2022 | Robison et al. |

OTHER PUBLICATIONS

United States Office Action, U.S. Appl. No. 17/397,674, Aug. 31, 2023, 26 pages.

PCT Invitation to Pay Additional Fees, PCT Application No. PCT/US22/38153, Oct. 13, 2022, 2 pages.

Muller, P. et al. "Adaptive Multichannel FES Neuroprosthesis with Learning Control and Automatic Gait Assessment." Journal of NeuroEngineering and Rehabilitation, vol. 17, Feb. 28, 2020, pp. 1-20.

* cited by examiner

ADAPTIVE STIMULATION ARRAY FOR MOTOR CONTROL

This disclosure relates generally to a mobility augmentation system, and more specifically to using a dynamically configurable array of electrodes to personalize and optimize mobility augmentation.

BACKGROUND

Augmenting a sequence of movements is a complex task that is more effectively accomplished when various types of movement augmentation such as electrical stimulation can be applied to different muscle groups at different times. Existing stimulation systems are limited in where they can provide stimulation since many have a limited number of electrode channels (i.e., a single anode/cathode pair). Furthermore, to stimulate different movements, existing systems require manual placement of electrodes at the necessary locations of the body. Hence, existing systems can only stimulate a number of independent movements equivalent to the number of electrode channels in the system. Existing systems also require manual effort to place the electrodes in the correct positions. An incorrect placement may be difficult to detect or correct, as the existing systems do not measure the quality of the stimulated movement to indicate that the placement is incorrect. Accordingly, a stimulation mechanism is needed that allows expressive control over how stimulation is applied through both the configuration and customization of stimulation and how the simulation functions (e.g., changing anode/cathode pairs).

SUMMARY

The wearable stimulation array and mobility augmentation system described herein enables personalized and dynamic movement stimulation. The wearable stimulation array includes an electrode multiplexer (MUX) that enables the dynamic reconfiguration of the array's electrodes to operate in one or more of various roles (e.g., anode, cathode, or disconnected). The mobility augmentation system applies a movement model (e.g., a machine learned model) to measurements taken by sensors at the wearable stimulation array. The model can determine an actuation instruction for each of various movements. For example, the model can determine electrical stimulation for each movement in a gait cycle, enabling an electrical signal to flow from one set of electrodes and to another set of electrodes, where the electrode configuration can change for each movement.

The mobility augmentation system can calibrate the wearable stimulation array such that default or generalized actuations are customized to the user wearing the array. For example, the mobility augmentation system can iterate through various electrical stimulations (e.g., reconfiguring electrode roles between anode and cathode, adjusting an amplitude of the electrical signal, etc.) and retrain the movement model using user feedback of the stimulated movements caused by the respective electrical stimulations. The mobility augmentation system can further optimize the actuation during use (e.g., between calibrations) by monitoring the stimulated movement and comparing the monitored movement to a target movement to adjust actuation to meet the user's current physical state. The wearable stimulation array can be integrated into an article of clothing for ease of use, and can be recalibrated upon initial wear to stimulate the contacted muscle group accordingly. These structural and functional features afford users movement stimulation that is personalized to the respective users, optimized over time as the user's body may change in behavior (e.g., due to fatigue or an onset of movement impairing symptoms), practical for daily use with apparel integration, and non-invasive for increased comfort and safety.

In one embodiment, a wearable stimulation array includes a set of configurable electrodes each configured to contact a different portion of a surface of a body of a user when the wearable stimulation array is worn by the user. The wearable stimulation array also includes a power source, a memory that stores a movement model representative of a set of movements, and a controller coupled to the set of configurable electrodes, the memory, and the power source. The controller is configured to, for a first movement of the set of movements, configure power from the power source to flow between a first electrode and a first set of electrodes such that the first electrode is configured to operate as an anode. The controller is also configured to, for a second movement of the set of movements, configure power from the power source to flow between the first electrode and a second set of electrodes such that the first electrode is configured to operate as a cathode.

The wearable stimulation array's controller may be further configured to determine each movement of the set of movements based on one or more of electromyography (EMG) data, inertial measurement unit (IMU) data, foot plantar pressure signals, or a context in which the movement occurs. The configured power may be an electrical signal and the controller may be further configured to adjust one or more of a frequency, an amplitude, or a pulse width of the electrical signal. The one or more electrodes of the set of configurable electrodes can be configured to alternate between providing stimulation and measuring EMG data. A movement of the set of movements may represent a phase of a gait cycle.

The wearable stimulation array may include sensors such as a heart rate sensor, IMU sensor, or pressure sensor coupled to the controller. The controller can receive measurements taken from the sensors and detect that the user is wearing the wearable stimulation array using the received measurements. In some embodiments, the controller can measure user activity data including one or more of galvanic skin response, heart rate, or respiration rate using the plurality of sensors. The controller can then determine a level of fatigue experienced by the user during movement using the measured user activity data and adjust the configured power based on the level of fatigue.

In some embodiments, the wearable stimulation array includes an IMU sensor or a foot pressure sensor. The controller can measure a movement using the IMU sensor or the foot pressure sensor and store data characterizing the measured movement. The stored data can be applied to the movement model to stimulate movement or used to characterize a movement profile of the user. The controller can also measure a movement stimulated by the wearable stimulation array, where the movement is measured using the IMU sensor or the foot pressure sensor. The controller can compare the measured stimulated movement to a predetermined movement representative of neurotypical movement, score the measured movement based on the comparison, and retrain the movement model based on the scoring.

The controller of the wearable stimulation array may be configured to create a training set that includes measured movement data associated with respective movement actuation instructions, where each movement actuation instruction specifies an electrical signal to be transmitted from a given electrode to a different electrode. The controller can then train the movement model using the training set. In some embodiments, the controller can retrain the movement model by receiving feedback from the user indicating a measure of approval of a movement stimulated by the wearable stimulation array and adjusting an association between the stimulated movement and an actuation instruction. For example, in response to the received feedback indicating the measure of approval of the stimulated movement is high, the controller may strengthen an association between the stimulated movement and an actuation instruction that enables an electrical signal from a first electrode to a second electrode. In the same example, in response to the received feedback indicating the measure of approval of the stimulated movement is low, weakening an association between the stimulated movement and the actuation instruction.

The wearable stimulation array's controller may be further configured to, for a third movement of the set of movements, configure power from the power source to flow between the first electrode to the second electrode via a first electrical signal and from a third electrode to a fourth electrode via a second electrical signal. The second electrical signal can be enabled by the controller responsive to enabling the first electrical signal, and a ratio of a pulse width of the first electrical signal to a pulse width of the second electrical signal is predetermined. In some embodiments, the controller can provide for display at a graphical user interface (GUI) information describing one or more of the configured power, the first set of electrodes, or the second set of electrodes. The controller can receive, via the GUI, a user selection of an electrode of the set of configurable electrodes to enable. In response to receiving the user selection, change one or more of the first set of electrodes or the second set of electrodes to include the user-selected electrode, and retrain the movement model based on the user selection.

The wearable stimulation array may further include a camera coupled to the controller. The camera may be configured to capture an image depicting movement by the user and provide the captured image to the controller, which can determine that the depicted movement is a movement within the set of movements. The controller may also determine that the user is performing the movement based on the captured image and movement data captured from an IMU sensor or a foot pressure sensor coupled to the wearable stimulation array. In one embodiment, the wearable stimulation array is coupled to a legging such that the set of configurable electrodes contacts a leg of the user. In another embodiment, the wearable stimulation array may be coupled to a sock or a shoe insole such that the set of configurable electrodes contacts a foot of the user.

In one embodiment, a method for calibrating a wearable stimulation array described herein includes initializing the wearable stimulation array, which includes multiple electrodes. A model can be accessed, where the model is configured to, for each movement of a set of movements, enable a corresponding electrical signal from a first set of the electrodes to a second set of the electrodes to stimulate the movement by the user. In response to the use of the accessed model to stimulate a movement of the set of movements by the user using the wearable stimulation array, feedback is received from the user indicating a measure of approval of the stimulated movement. The wearable stimulation array is calibrated by retraining the accessed model based on the received feedback to change, for at least the stimulated movement of the set of movements, one or more of the corresponding electrical signal, the first set of electrodes, and the second set of electrodes.

The measured movement data may be representative of neurotypical movement measured from a general population of users. The model can be trained using a training set with measured movement data associated with respective actuation instructions. To re-train the accessed model based on the received feedback, an association between stimulated movement and an actuation instruction may be adjusted (e.g., strengthening or weakening the association based on a measure of approval of the stimulated movement).

The model can be configured to enable the corresponding electrical signal based on one or more of EMG data, IMU data, foot plantar pressure signals, a level of fatigue of a measured movement, or a context in which the stimulated movement is to occur. A context in which the stimulated movement is to occur can be determined based on one or more of the user, a location of the wearable stimulation array on the user's body, a time of day or a location of the user. The model may be configured to enable the corresponding electrical signal based on the determined context. EMG data can be measured using one of more of the electrodes, where the model is configured to enable the corresponding electrical signal based on the EMG data.

The user's movement can be measured using one or more of IMU sensors or foot pressure sensors of the wearable stimulation array. The measured movement may include measured forces from the user's joints. The data characterizing the measured movement can be stored and applied to the model to stimulate the movement or used to characterize a movement profile of the user. In some embodiments, the measured movement can be compared to a predetermined movement representative of fatigue affecting the movement. A level of fatigue of the measured movement may be determined based on the comparison, where the model is configured to enable the corresponding electrical signal based on the level of fatigue.

In some embodiments, electrical signals can be determined by changing one or more of a frequency, an amplitude, or a pulse width of the corresponding electrical signal used to stimulate movement. The electrical signals can be sequentially enabled through permutations of pairs of the electrodes. A pause can occur between successive enabling of electrical signals of the electrical signals to allow the user to provide feedback of the movement stimulated by an enabled electrical signal. The wearable stimulation array can be calibrated by retraining the accessed model based on the received feedback of the movement stimulated by the electrical signals. In some embodiments, the wearable stimulation array can be calibrated by tracking a user's progress in performing a movement without help from the array. User movements can be measured using sensors of the wearable stimulation array, where the user movements represent the user performing a given movement without stimulation. A movement progress can be determined using the measured user movements, and the accessed model can be retrained further based on the movement progress.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

System Architecture

Figure 1:
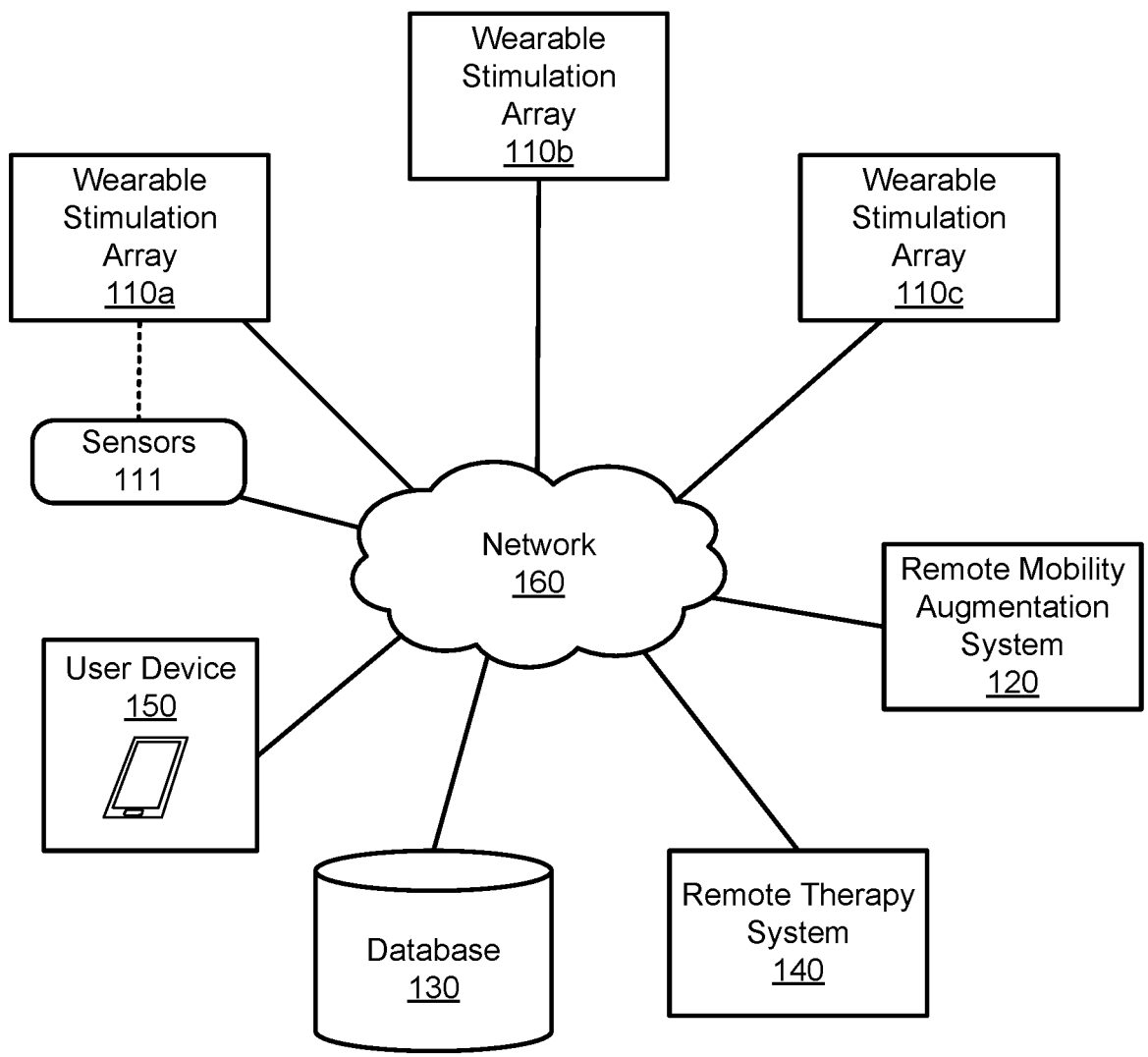
FIG. 1 is a block diagram of a system environment in which a wearable stimulation array operates, in accordance with at least one embodiment.

FIG. 1 is a block diagram of a system environment 100 in which a wearable stimulation array operates, in accordance with at least one embodiment. The system environment 100 shown by FIG. 1 includes wearable stimulation arrays 110a-c, sensors 111, a remote mobility augmentation system 120, a database 130, a remote therapy system 140, a user device 150, and a network 160. The system environment 100 may have alternative configurations than shown in FIG. 1, including for example different, fewer, or additional components. For example, the remote therapy system 140 may be omitted from the system environment 100 without compromising the functionality of the wearable stimulation arrays 110a-c.

The system environment 100 enables personalized and dynamic movement augmentation. Each wearable stimulation array is configured to apply actuation that is optimized based on the user's feedback of the actuation. For example, the wearable stimulation array can calibrate default actuation depending on their effects on the user. The array may iterate through a variety of actuations for a movement and allow the user to provide feedback indicating which of the actuations is preferred for the movement (e.g., the most comfortable or effective). The array may perform this iterative calibration for multiple movements, such as the movements within a gait cycle. The array can iterate through actuations by automatically adjusting, for example, parameters of an electrical signal and which of the electrodes of the array operate as anodes or cathodes. In this way, the array receives user feedback for various actuation of a variety of movements and can maintain scores based on the feedback for each attempted actuation. The highest scoring actuation can replace a default actuation to customize the array to the user. The present wearable stimulation array provides the advantage of actuation adjustment without requiring a user to manually change the electrodes or the placement of the electrodes.

Additionally, the wearable stimulation array can continue to adapt to the user's body during use (e.g., between calibrations), which can change over time due to fatigue, age, injury, or any other stimulus that affects physical movement. For example, the array can determine the efficacy of an actuation by comparing the resultant stimulated movement to a target movement (e.g., a neurotypical movement or a baseline for the user during calibration). The array can use the comparison as feedback to retrain a model that determines the actuation to apply, and iterate through various actuations until the resultant stimulated movement is within an acceptable range of the target movement. Yet another benefit of the wearable stimulation array is that the electrical stimulation applied by the array may be applied at the surface of the user's skin, improving the safety and comfort of using the array over invasive stimulation devices with needles that penetrate into the user's muscles. Thus, through calibration, automated actuation adjustment, and continued optimization, the wearable stimulation array described herein can provide personalized, non-invasive, and dynamic movement augmentation.

The wearable stimulation arrays 110a-c applies electrical stimulation or other types of actuation to increase the mobility of its users. The wearable stimulation arrays 110a-c monitor a user's movement to determine current movement (e.g., using IMUs or pressure sensors) or intended movement (e.g., using EMG sensors), and applies actuation based on the monitored movement. The arrays 110a-c may be worn by one or more users. For example, a single user may wear the arrays 110a-c at a forearm, a shank, and a foot, respectively. In another example, a first user may wear the arrays 110a-b and a second user may wear the array 110c. A wearable stimulation array may include sensors or be communicatively coupled to a sensor. For example, the wearable stimulation array 110a is communicatively coupled to the sensor 111, which may be a camera configured to capture image data of the user's movement for determining an appropriate actuation instruction.

The wearable stimulation arrays 110a-c may be worn at various locations on the body of the user to monitor and stimulate movement. For example, the wearable stimulation array 110a may use electromyography to monitor the electrical activity of the user's muscles. From the monitored electrical activity, the array 110a may determine a corresponding actuation for stimulating movement using a movement model (e.g., a machine learning model) trained to identify an actuation from movement data. The terms "movement data" or "movement signal" may refer to data such as kinematic, kinetic, or pressure signals representing a user's physical movement. As referred to herein, "activity data" represents activity of the user's body such as physical movement, electrical muscle activity, heart rate, respiration, any suitable measurement of current movement or intended movement, or combination thereof. Activity data may include movement data. Continuing the earlier example, the array 110a may determine an actuation to apply based on the identified intention. The determined actuation may include instructions to apply electrical stimulation to the various locations on the body of the user. For example, the array 110a at the left shank may be communicatively coupled to the array 110b at the right shank, and the actuation determined by the array 110a may instruct the array 110a to apply a first electrical signal and the array 110b to apply a second electrical signal.

The wearable stimulation arrays 110a-c enable both personalization and optimization of mobility augmentation for their users. The arrays 110a-c may calibrate the actuation to the user's body and continually optimize the actuation as the user wears the arrays. To calibrate the actuation, the arrays 110a-c may first apply a default actuation instruction for respective movements with which they are configured to stimulate. The user may provide feedback for each default actuation instruction (e.g., a measure of approval indicating comfort or efficacy of the actuation), and the arrays 110a-c may use the feedback to modify the actuation until the user feedback indicates that the actuation is satisfactory.

In addition to personalized calibration, another way in which the wearable stimulation arrays 110a-c personalize mobility augmentation is by using movement data collected from a user to train a user-specific machine learning model used to determine the actuation for that user's movements. The arrays 110a-c may optimize mobility augmentation by measuring the success of the actuation in real time (e.g., user feedback) and in response, re-training the machine learning model using the feedback and modifying the subsequently applied actuation. Personalization and optimization will be described in further detail throughout the description of the mobility augmentation system 220 in FIG. 2.

The remote mobility augmentation system 120 receives and processes data from the wearable stimulation arrays 110a-c. The data received from the arrays 110a-c may include movement data, applied actuation, and user feedback. This data may be used to generate new actuation instructions or modify existing actuation instructions. The remote system 120 may use the processed data to provide actuation instructions for the arrays 110a-c to execute. The remote mobility augmentation system 120 may have functionality similar to that of the mobility augmentation system 220 described in FIG. 2. The remote system 120 may be hosted on a server or computing device (e.g., a smartphone) that communicates with the wearable stimulation arrays 110a-c via the network 160.

In some embodiments, the remote mobility augmentation system 120 trains and applies one or more machine learning models configured to determine an actuation instruction based on measured movement data. The remote mobility augmentation system 120 may maintain machine learning models in addition to or alternative to the wearable stimulation arrays 110a-c maintaining the models. In one embodiment, the remote mobility augmentation system 120 trains the models based on movement data collected by the arrays 110a-c. The arrays 110a-c send, via the network 160, movement data to the remote mobility augmentation system 120 and leverage the trained machine learning models to receive, from the remote mobility augmentation system 120, an actuation instruction determined by the one or more models. The remote mobility augmentation system 120 may maintain models that are generalized to movement across a population or customized to a particular user, movement type, any suitable phenotypic trait, or a combination thereof. The training and application of machine learning models used for augmenting mobility is further described in the description of FIG. 2.

The actuation for movement stimulation may be determined by the wearable stimulation arrays 110a-c, the remote mobility augmentation system 120, or manually specified by an operator (e.g., a physical therapist via remote therapy system 140) or the user through an input interface on the user device 150. In some embodiments, the actuation includes electrical stimulation (e.g., a functional electrical stimulation (FES) signal) characterized by a frequency, a pulse duration, duty cycle, and an amplitude (e.g., a value of current in milliamperes). The wearable stimulation array 110a-c may enable various actuation types. Examples of actuation types include manually triggered actuation, amplification, contralateral replay, body-to-body coaching, templated sequencing, and responsive optimization. Examples of actuation by a wearable device may be found in U.S. patent application Ser. Nos. 17/113,058 and 17/113,059, filed on Dec. 6, 2020, which are incorporated herein by reference.

The database 130 stores data related to the operation of the wearable stimulation arrays 110a-c. In some embodiments, the database 130 stores data for training machine learning models of the wearable stimulation arrays 110a-c or the remote mobility augmentation system 120. The data stored in the database 130 may include labeled or unlabeled movement data and labels associated with movements, or templates associated with sequences of muscle firings for given movements. The mobility management system 110 or the mobility augmentation devices 120a and 120b may access the stored data to train machine learning models. The wearable stimulation arrays 110a-c may provide their measured data to the database 130. The provided data may be organized in a data structure including the measured data, biographical information identifying the user and phenotypic traits, and a label identifying an actuation instruction to augment a movement corresponding to the measured data.

In some embodiments, the database 130 stores users' individual movement models in addition to a general model trained on data from across a population. The wearable stimulation arrays may access a model stored in the database 130. For example, a first user who is a stroke survivor may access the movement model of a second user's, who was also a stroke survivor, to begin calibration and optimization from the second user's model rather than a more general movement model that is not yet adapted for stroke survivors.

The remote therapy system 140 enables a third party (e.g., a medical professional or athletic coach) to monitor the user's movement and analyze the information to further augment the user's movement. For example, a physician uses the remote therapy system 140 to monitor their patient's movement and adjust a combination of actuation instructions upon identifying that the patient's movement is not improving under the current actuation instructions. The remote therapy system 140 may be a software module that the third party may execute on a computing device (e.g., a smartphone). In some embodiments, the remote therapy system 140 is a standalone device that may be communicatively coupled to the wearable stimulation arrays 110a-c to manually adjust or generate actuation instructions used to augment the user's movements (e.g., overriding the actuation instructions determined by the wearable stimulation array). The remote therapy system 140 may include an input interface for the third party to specify parameters of an actuation instruction (e.g., the amplitude and frequency of FES signals) and when to apply them.

The remote therapy system 140 may provide actuation strategies to be applied by the mobility augmentation system 220. In some embodiments, a user of the remote therapy system 140 (e.g., a therapist) may specify when to apply stimulation and through which of the wearable stimulation arrays 110a-c to apply stimulation. For example, the therapist may define where, when, and how (e.g., parameters of electrical signals) to stimulate the patient's gait based on a video camera of the sensors 111 that captures the patient's gait. The therapist-specified actuation strategy may be communicated from the remote therapy system 140 to the wearable stimulation arrays 110a-c over the network 160.

The user device 150 may be a personal computer (PC), a tablet PC, a smartphone, or any suitable device capable of executing instructions that specify actions to be taken by that device. The user device 150 may include a processor (e.g., a central processing unit (CPU), a graphics processing unit (GPU), a digital signal processor (DSP), one or more application specific integrated circuits (ASICs), one or more radio-frequency integrated circuits (RFICs), or any combination of these), a memory, a user interface to receive user inputs or provide outputs to the user (e.g., a visual display interface including a touch enabled screen, a keyboard, microphone, speakers, etc.). The visual interface may include a software driver that enables displaying user interfaces on a screen (or display).

The network 160 may serve to communicatively couple the wearable stimulation arrays 110*a-c*, the sensor 111, the remote mobility augmentation system 120, the database 130, the remote therapy system 140, and the user device 150. For example, the wearable stimulation array 110*a* and the remote therapy system 140 are configured to communicate via the network 160. In some embodiments, the network 160 includes any combination of local area and/or wide area networks, using wired and/or wireless communication systems. The network 160 may use standard communications technologies and/or protocols. For example, the network 160 includes communication links using technologies such as Ethernet, 802.11, worldwide interoperability for microwave access (WiMAX), 3G, 4G, 5G, code division multiple access (CDMA), digital subscriber line (DSL), etc. Examples of networking protocols used for communicating via the network 160 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network may be represented using any suitable format, such as hypertext markup language (HTML) or extensible markup language (XML). In some embodiments, all or some of the communication links of the network 160 may be encrypted using any suitable technique or techniques.

Although the components of the system environment 100 are shown as connected over the network 160, one or more components may function without being connected to the network 160. For example, the wearable stimulation arrays 110*a-c* may function offline when the arrays 110*a-c* are not able to connect to the network 160. When the arrays 110*a-c* are able to reconnect to the network 160, they may upload measured movement data and corresponding actuation instructions performed to the remote mobility augmentation system 120 or the remote therapy system 140 via the network 160.

Wearable Stimulation Array

Figure 2:
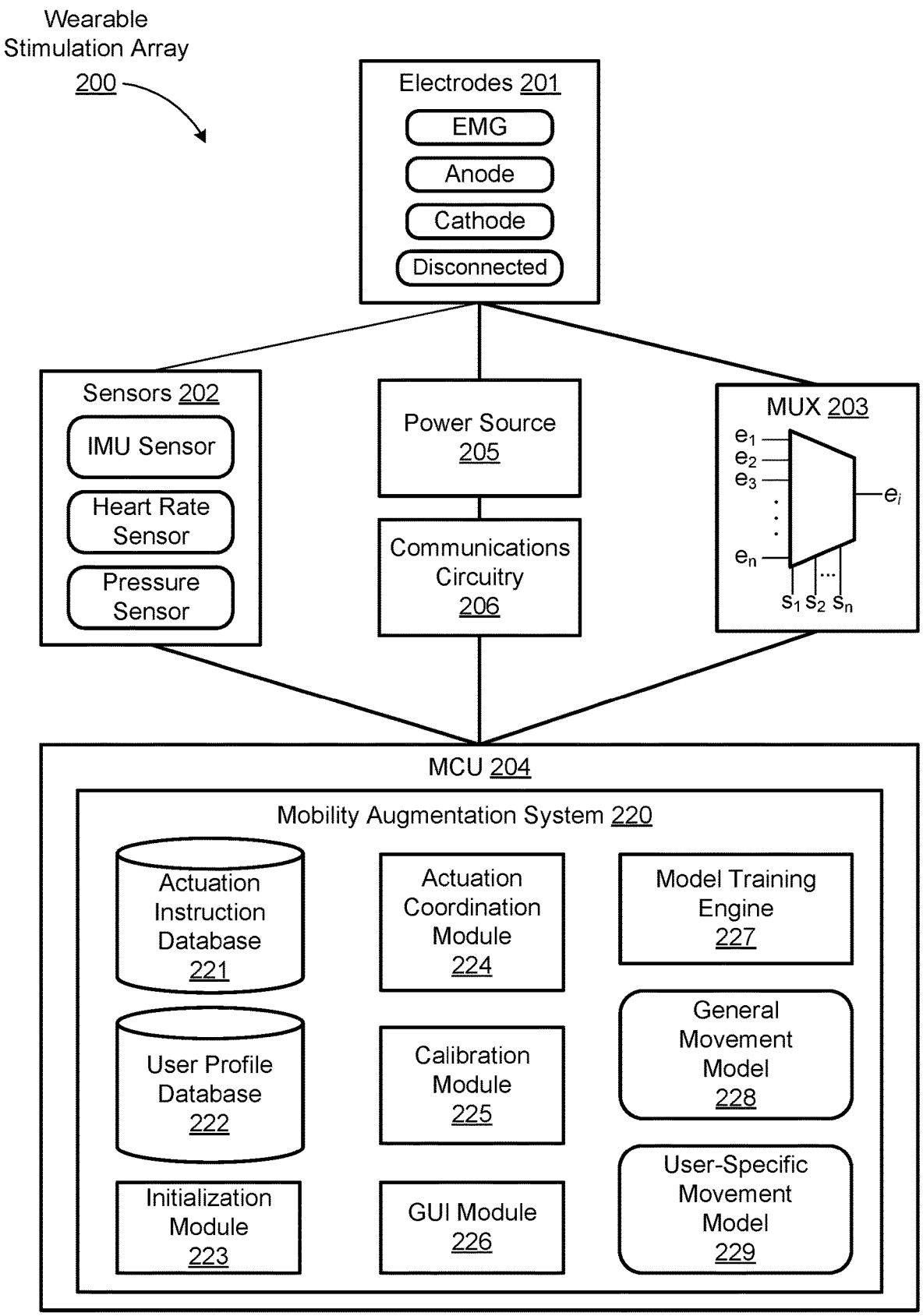
FIG. 2 is a block diagram of a wearable stimulation array, in accordance with at least one embodiment.

FIG. 2 is a block diagram of a wearable stimulation array 200, in accordance with at least one embodiment. The wearable stimulation array 200 includes electrodes 201, sensors 202, an electrode multiplexer (MUX) 203, a microcontroller (MCU) 204, a power source 205, and communications circuitry 206.

The electrodes 201 deliver electrical stimulation to the user of the wearable stimulation array 200. The electrodes 201 may be transcutaneous electrodes for electrical nerve stimulation. Each electrode may be coupled to one or more pads that contact the user's skin to deliver an electrical signal. The placement of the pads of respective electrodes may be spaced apart such that an actuation applied within a proximity (e.g., at the same muscle) of another actuation does not interfere with the other actuation. Alternatively, the MCU 204 may determine which electrodes to apply the electrical stimulation through based on the locations of the electrodes. For example, if electrode ID nos. 1 and 2 are within an inch of one another and electrode ID no. 3 is four inches from both electrodes 1 and 2, the MCU 204 may determine to choose electrode 3 and one of electrodes 1 or 2 as the cathode electrodes such that the two electrical signals do not interfere with one another. The size of the electrode pad may be sized to decrease the likelihood of causing the user pain during stimulation. For example, an electrode pad contacting the skin may have a 24 millimeter (mm) diameter. In some embodiments, the electrodes 201 includes electrodes for sensing EMG data of the user. The electrodes may be surface or skin electrodes, which are non-invasive and structured to adhere to the surface of the skin without penetrating the skin to determine electrical activity when the user's muscles are stimulated.

The electrodes 201 may include two or more electrodes. In one example, the wearable stimulation array 200 may be a 24-electrode array, where the electrodes 201 consist of 24 electrodes. An electrode may serve as a cathode or an anode. For example, the electrodes 201 may form an 8-electrode array that includes two cathodes and six anodes. Additionally, the electrode may be disconnected or off, where it is unselected to be either an anode or cathode. For example, in an 8-electrode array, six electrodes may function as cathodes or anodes while two electrodes are disconnected and do not serve as either a cathode or anode. In some embodiments, an electrode of the electrodes 201 may be used to sense EMG signals. Each electrode of the electrodes 201 may be associated with an identifier (e.g., an identification number). The identifiers may be used in an actuation instruction to identify which electrodes are used during a given actuation instruction. For example, to stimulate a knee extension, electrode ID no. 1 may be used as an cathode and electrode ID nos. 4 and 5 may be used as an anode. The identifiers may also be used to identify which electrodes are used to perform EMG sensing. For example, electrode ID nos. 2 and 3 may be used to perform EMG sensing while the electrodes in the previous example stimulate a knee extension. The wearable stimulation array 200 may be initialized with a default electrode combinations used for actuation or EMG sensing or may be initialized with combinations modified by the user. For example, after a calibration, the user changes the default combinations of electrodes and the new combination is saved in the memory (e.g., the user profile database 222) of the MCU 204 for subsequent initializations of the wearable stimulation array 200.

The mobility augmentation system 220 (e.g., the actuation coordination module 224) may reconfigure the roles of the electrodes 201. The roles of the electrodes may be reconfigured depending on the movement intended to be stimulated or the feedback provided by the user. For example, to stimulate a knee extension, a first set of electrodes may be configured as anodes and a second set of electrodes may be configured as cathodes. To enable an electrode to alternate between an anode or a cathode, the mobility augmentation system 220 may alternate the direction of the current drawn from the power source 205. In the previous example, the first set of electrodes may be configured as cathodes and the second set of electrodes may be configured as anodes to stimulate a different movement (e.g., a knee flexion). The mobility augmentation system 220 may also adjust the role of an electrode to serve as an EMG sensing electrode. For example, the mobility augmentation system 220 may enable a connection between an electrode and an EMG sensor. The EMG sensor may be included in the sensors 202 although not depicted as such. In addition to reconfiguring the roles of the electrodes 201, the mobility augmentation system 220 may select which electrodes are activated for each actuation instruction or EMG sensing operation. This selection is further described in the description of the MUX 203.

The wearable stimulation array 200 may be coupled to an article of clothing for routine use. For example, the wearable stimulation array 200 may be incorporated into a legging such that a set of configurable electrodes (i.e., the electrodes 201) contacts a leg of the user. In another example, the array 200 is coupled to a sock or a shoe insole such that the set of configurable electrodes contacts a foot of the user. The wearable stimulation array 200 may have various wearable form factors such as exoskeletons, modular electrode straps, leggings, foot pressure beds, any wearable form factor suitable for targeting a particular muscle group on a user's body, or a combination thereof.

The sensors 202 measure the user's movement or body measurements related to movement (e.g., heart rate or respiration rate affected by movement). The movement can be measured before, during, or after application of an actuation (e.g., electrical stimulation). Movement measured before actuation may be used to determine which actuation instruction to enable. Movement measured during or after the application of the actuation may be used to score the applied actuation. The sensors 202 may be one or more of a microelectromechanical systems (MEMS) device, IMU, pressure sensor bed, EMG sensor, heart rate sensor, force sensor, or any suitable device for measuring kinetic or kinematic signals produced by a muscle. The sensors 202 may include an EMG sensor, which may include dedicated electrodes (i.e., separate from the electrodes 201) for collecting EMG data, or the wearable stimulation array 200 may obtain EMG data from the electrodes 201. The sensors 202 may include a galvanic skin sensor, which may include dedicated electrodes for measuring changes in sweat gland activity on the skin or may use the electrodes 201 to collect the galvanic skin response data.

The sensors 202 may be located at various locations on the user's body. For example, a pressure sensor bed may be placed in the user's right shoe to measure the user's right foot pressure as the user completes a gait. A set of sensing electrodes may be placed at the shank of the user's right leg to measure the intended movement data before and during the gait. The sensors 202 may be communicatively coupled to the MCU 204 to provide the measured data for determining or optimizing actuation instructions applied by the wearable stimulation array 200. In some embodiments, the locations of the sensors 202 includes the joints of the body (e.g., ellipsoid joint and saddle joint). For example, the sensors 202 may measure movement at the ellipsoid and saddle joints IMU's to determine the quality of a user's grip (e.g., how far the user is able to close their hand into a fist).

The sensors 202 may include a sensor that is not co-located with the wearable stimulation array 200 (e.g., the sensors 111). For example, the sensors 202 may include a camera directed at the user and configured to capture image data of the user's movements. The camera may be communicatively coupled to the wearable stimulation array 200 to provide the image data to the MCU 204 (e.g., to the mobility augmentation system 220), which determines an actuation signal to help stimulate the movement depicted in the image or expected to follow the movement depicted in the image. In another example, the sensors 202 may include a sensor to measure strength of a user's grip such as a handgrip dynamometer. The dynamometer may be communicatively coupled to a wearable stimulation array that is worn at the user's hand or forearm, and the measurements from the dynamometer and sensors at the array may be used to adjust actuation instructions to assist the user in gripping objects.

The MUX 203 enables the wearable stimulation array 200 to select a particular combination of the electrodes 201. The selection of electrodes may be performed over time, over particular phases of a movement, any suitable division of stages that may require a different combination of electrodes per stage, or a combination thereof. Although a single MUX is shown in FIG. 2 to maintain clarity in the illustration, the wearable stimulation array 200 may include more than one MUX that functions similar to the MUX 203. The MUX 203 may be coupled to the power source 205, a sensor of the sensors 202 (e.g., an EMG sensor), the MCU 204, and the electrodes 201. The MUX 203 may receive selection signals (e.g., $s_1$, $s_2$, etc.) generated by the MCU 204. For example, the actuation coordination module 224 may determine an actuation instruction to apply to stimulate a movement, where the actuation instructions specify a combination of electrodes. The MCU 204 may enable the specified combination to be selected by activating a corresponding combination of the selection signals input to the MUX 203.

To use the MUX 203 to select a combination of electrodes 201 that varies over time, the MCU 204 may outputs a corresponding combination of selection signals that changes over time. The selection of various electrodes over time may be applicable to stimulate a sequence of movements known to occur in the sequence (e.g., a gait cycle). For example, a gait cycle's swing phase can begin at a toe-off, proceed to a mid-swing, and end with a terminal swing. The MCU 204 may access default actuation instructions to calibrate the user's swing phase movements, where each default instruction includes one or more corresponding selection signals to activate the electrodes 201. For example, in an 8-electrode array, there may be two MUX's each having two selection signals $s_1$ and $s_2$. To stimulate the toe-off, the MCU 204 may provide selection signal values of 0 and 1 for the respective selection signals $s_1$ and $s_2$ to a first MUX to select electrode ID no. 2 as the cathode, where the first MUX is couple to electrodes 1-4. Further, the MCU 204 may provide selection signal values of 0 and 1 for the respective selection signals $s_1$ and $s_2$ to a second MUX to select electrode ID no. 6 as the anode, where the second MUX is coupled to electrodes 5-8. Following the toe-off stimulation, the MCU 204 may change the selection signal values provided to the two MUX's to stimulate the mid-swing movement and finally, may further change the selection signal values to stimulate the terminal swing.

The MCU 204 represents one or more processors such as a microprocessor, a central processing unit, or the like. More particularly, the processing device may be complex instruction set computing (CISC) microprocessor, reduced instruction set computing (RISC) microprocessor, very long instruction word (VLIW) microprocessor, or a processor implementing other instruction sets, or processors implementing a combination of instruction sets. The MCU 204 may also be one or more special-purpose processing devices such as an application specific integrated circuit (ASIC), a field programmable gate array (FPGA), a digital signal processor (DSP), network processor, or the like. The MCU 204 may be configured to execute instructions for performing the operations and steps described herein.

The MCU 204 hosts and executes a mobility augmentation system 220, which includes software modules such as an initialization module 223, an actuation coordination module 224, a calibration module 225, a GUI module 226, and a model training engine 227. The mobility augmentation system 220 includes models for determining actuation (e.g., electrical stimulation) instructions such as a general movement model 228 and a user-specific movement model 229. The mobility augmentation system 220 includes databases such as an actuation instruction database 221 and a user profile database 222. The mobility augmentation system 220 may have alternative configurations than shown in FIG. 2, including different, fewer, or additional components. For example, one or more of the databases 221 or 222 may be stored remotely rather than on a memory of the MCU 204 at the wearable stimulation array 200 (e.g., contents stored in the database 130) and may be accessible through the network 150. In another example, an additional report generation module may generate a report of the applied actuation and the monitored movement data associated with the actuation and provide the report to the remote therapy system 140.

The actuation instruction database 221 stores actuation instructions for enabling the wearable stimulation array 200 to stimulate a user's movement. An actuation instruction may specify an actuation type, duration of actuation, location on a wearable stimulation array at which the actuation is to occur, any suitable parameter of the actuation (e.g., amplitude, frequency, etc.), or combination thereof. An actuation types classifies the actuation into a manner of actuation such as electric, mechanic, haptic, audio, visual, pneumatic, hydraulic, or a combination thereof. The duration of actuation may vary from short (e.g., ten milliseconds) to long (e.g., ten seconds) durations. The duration may vary based on the actuation type. For example, electrical stimulation may last shorter than audio actuation. The location of actuation may indicate which hardware components of the wearable stimulation array output or apply the actuation. For example, the location of actuation may be a particular electrode of the electrodes 201.

In a first example, an actuation instruction specifies that an electrical signal is enabled from a first set of electrodes of the electrodes 201 to a second set of electrodes of the electrodes 201. The actuation instruction may further specify that the electrical signal is to have a duration of 0.5 seconds, a rectangular pulse with a frequency of 100 Hz and an amplitude of 20 mA, and a location of actuation includes the first set of electrodes designated as cathodes (e.g., electrode ID no.'s 1 and 8) and the second set of electrodes designated as anodes (e.g., electrode ID no.'s 2-7).

Actuation instructions may include a combination of different types, durations, and locations. In a second example, an actuation instruction specifies that a first electrical signal is enabled from a first set of electrodes (e.g., electrode ID no. 1) to a second set of electrodes (e.g., electrode ID no.'s 2-4). In addition, actuation instructions of the second example also specify that a second electrical signal is enabled from a third set of electrodes (e.g., electrode ID no. 8) to a fourth set of electrodes (e.g., electrode ID no.'s 5-7). Further yet, the actuation instructions of the second example specify that a haptic actuation (e.g., a vibration) occurs after the electrical stimulation finishes.

Actuation instructions may involve multiple wearable stimulation arrays. In a third example, two wearable arrays may be communicatively coupled over a network to receive instructions that enable simultaneous stimulation at the two arrays. The simultaneous stimulation may be identical or different. For example, the two arrays may be located such that they contact both of the user's shanks. To assist the user with a jumping motion, which may require identical stimulation at both shanks, the two arrays may be instructed to perform the same actuation at the same time. To assist the user with a walking motion, which may require stimulation that is similar in various aspects except for timing, a first array at the user's left leg may be instructed to perform an actuation first and the second array at the user's right leg may be instructed to perform the same actuation after sensors at the first array determine that the stimulated movement at the left leg is finished and transmit a notice to the second array. The instructions may be generated by a mobility augmentation system onboard an MCU of one of the stimulation arrays and communicated to the other array's MCU via a network. Alternatively or additionally, the instructions may be generated by a remote mobility augmentation system at a cloud-based server and is communicated to both arrays via a network.

The user profile database 222 stores information regarding one or more users. The users may be users of the wearable stimulation array having memory to store the user profile database 222. In some embodiments, information of users of the wearable stimulation arrays transmitted to the user profile database 222, which is located at a remote server such as the remote mobility augmentation system 120. The user profile database 222 may include user information such as body measurements (e.g., height, weight, body mass index, body temperature, heart rate, galvanic skin response, etc.) and movement measurements (e.g., walking pace, steps taken, elevation gain, exercises performed). Such user information may be provided by the user manually (e.g., the user entering their height) or tracked by a wearable device such as the stimulation array described herein or a wearable fitness tracker (e.g., a smartwatch).

The user information stored in the user profile database 222 may also be tracked by sensors (e.g., the sensors 202 of the wearable stimulation array 200). For example, the user profile database 222 may store a record of the movement data representing stimulated movement of the user by the wearable stimulation device 200. In some embodiments, the user profile database 222 stores feedback from the user indicating a measure of approval of the stimulated movement. The feedback may be inferred through measurements taken by the wearable stimulation array 200 or manually provided by the user. For example, the wearable stimulation array 200 measures and compares stimulated movement from two different actuation instructions intended to stimulate the same movement (e.g., a dorsiflexion). The wearable stimulation array 200, which may be located at the user's shoe, measures kinetic movement data representing the dorsiflexions of differing qualities stimulated by the two actuation instructions. The wearable stimulation array 200 compares the kinetic movement data of the stimulated movements to kinetic movement data of a neurotypical dorsiflexion and determines that the first actuation instruction stimulated movement that is more similar to neurotypical movement than the second actuation instruction stimulated.

Figure 5:
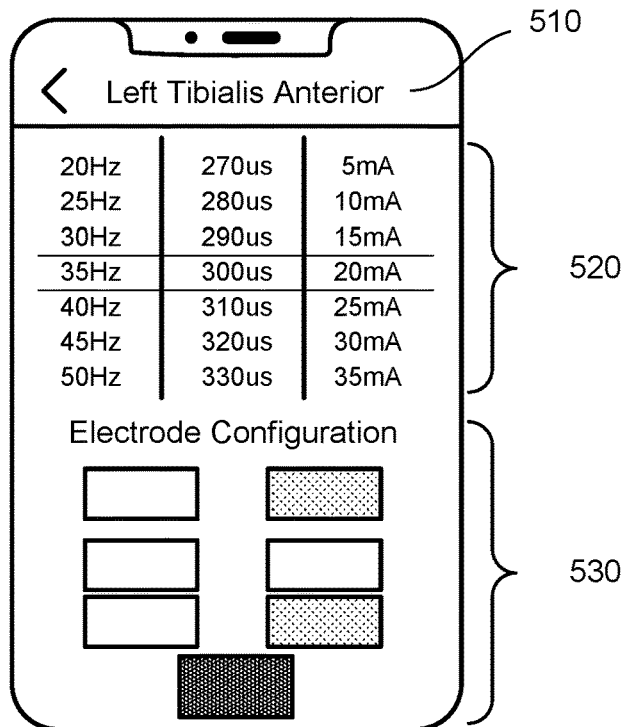
FIG. 5 depicts graphical user interfaces (GUIs) for managing electrical stimulation by a wearable stimulation array, in accordance with at least one embodiment.
Figure 5:
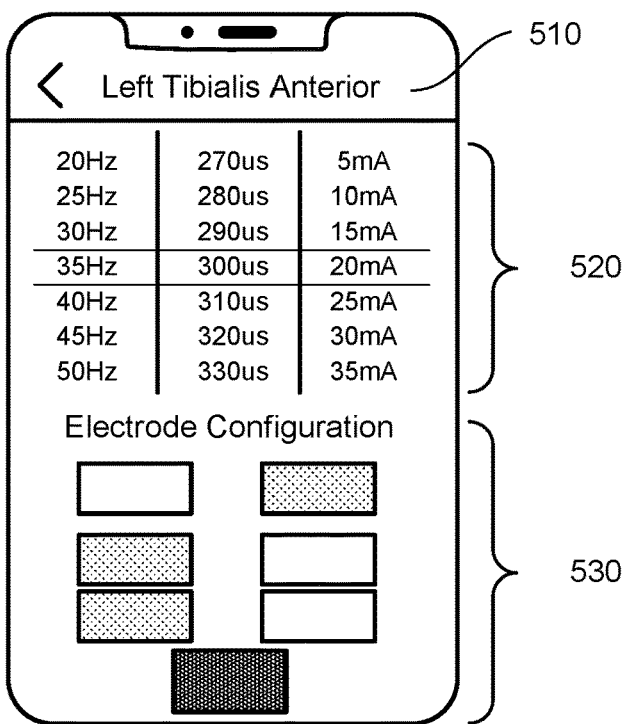
Figure 6:
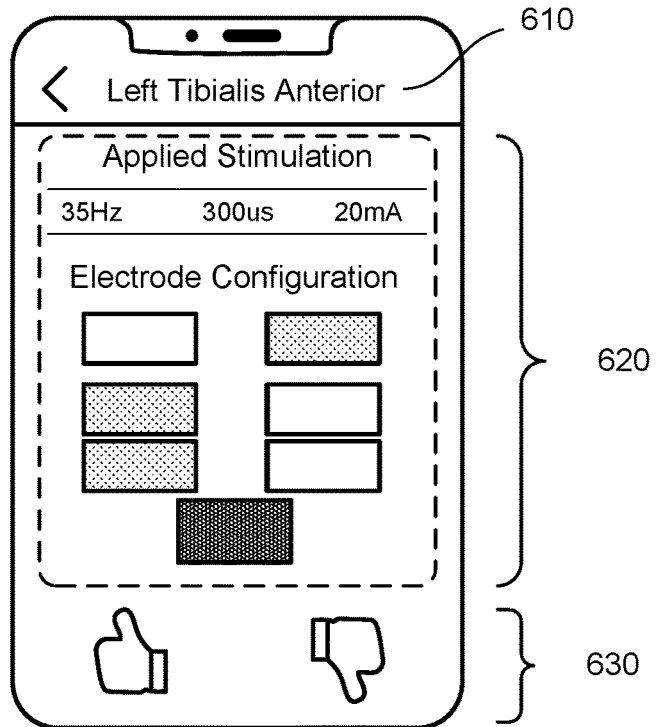
FIG. 6 depicts GUIs for providing feedback of stimulated movement provided by a wearable stimulation array, in accordance with at least one embodiment.
Figure 6:
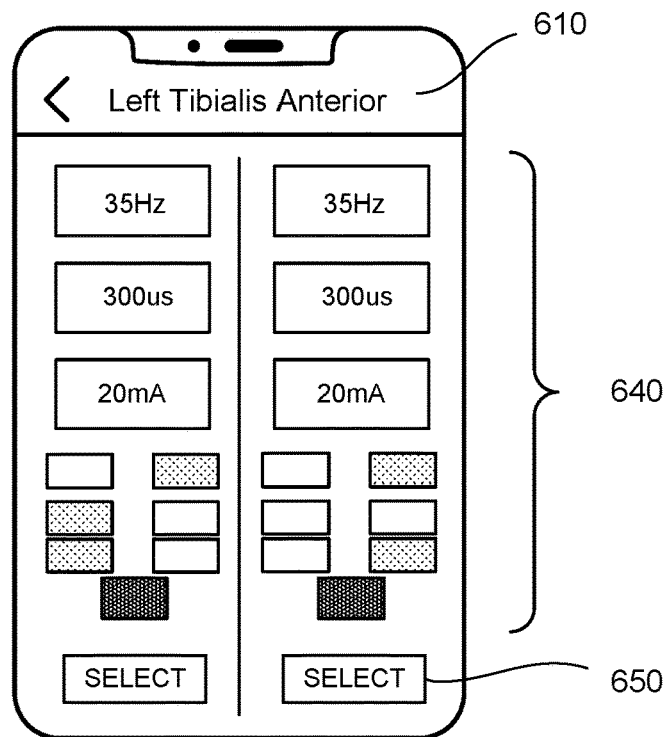

In another example, a user manually provides feedback that is stored in the user profile database 222. The wearable stimulation device 200 may be communicatively coupled to a user device (e.g., the user device 150) through which the user can provide feedback indicating a measure of comfort or effectiveness of the actuation by the wearable stimulation device 200. An example GUI through which a user can provide feedback indicating a measure of comfort or effectiveness is shown in FIG. 6. In some embodiments, user-provided feedback stored in the user profile database 222 includes feedback indirectly provided by the user through a user interface. For example, the user adjusts the actuation instruction via a GUI on a user device communicatively coupled to the wearable stimulation array 200. The user profile database 222 may store the user's chosen actuation modification and link the modification to the stimulated movement such that subsequent array-actuated stimulations of the movement can reference the user's modification stored in the database 222. An example GUI through which the user can adjust an actuation instruction is shown in FIG. 5.

The initialization module 223 initializes the wearable stimulation array 200. The initialization module 223 may help conserve power of the wearable stimulation array 200 that is not necessarily attached to a steady power source (i.e., the array 200 may be a wireless device). For example, the initialization module 223 may pause functions such as sensing the user's muscle firings (e.g., by determining EMG signals via the electrodes 201 or sensing movement data via the sensors 202) after the module 223 determines that a user is not wearing the wearable stimulation array 200 and resume the functions after the module 223 determines that the user has resumed wearing the array 200. The initialization module 223 may determine whether the user is wearing the array 200 using sensors (e.g., the sensors 202 or a remote sensor such as a camera communicatively coupled to the MCU 204). For example, the initialization module 223 uses data from a heart rate sensor of the sensors 202 to determine that no heart rate has been sensed for more than a predetermined time threshold (e.g., 10 seconds) and thus, the user has removed the wearable stimulation array 200. Similarly, the module 223 may determine that a heart rate has been detected a minimum number of times (e.g., 5 times) within a threshold period of time (e.g., 8 seconds) and thus, the user has worn the wearable stimulation array 200.

The actuation coordination module 224 enables or disables actuation applied through a wearable stimulation array. The actuation coordination module 224 can determine likely movements (e.g., ankle dorsiflexion) to determine a corresponding actuation to apply. The actuation coordination module 224 may determine a movement based on EMG data, IMU data, foot plantar pressure signals, a context in which the movement occurs, any suitable data through which movement can be inferred, or a combination thereof. The module 224 may use one or more of the aforementioned data types to determine a movement of a set of movements with which a wearable stimulation array is configured to assist the user. Example movements may include those within a gait cycle which as a heel strike, loading response, mid-stance, terminal stance, pre-swing, toe-off, mid-swing, and terminal swing. The term "movement" used herein may refer broadly to an activation of a particular muscle group to move or maintain a position. For example, standing may be a type of movement that the wearable stimulation array described herein may assist in despite minimal to no movement relative to other movements such as walking or running.

The actuation coordination module 224 can determine a movement using EMG data to enable a corresponding actuation instruction. For example, upon identifying, based on measured EMG signals, a muscle firing event corresponding to a kinematic signal associated with a toe lift of the user's contralateral foot, the module 224 may apply an actuation instruction associated with a toe lift from a contralateral foot. The actuation coordination module 224 may receive EMG data from electrodes of the wearable stimulation array that are configured to sense EMG signals of muscle firing events. Alternatively or additionally, the user may be wearing electrodes (e.g., multiple wearable stimulation arrays) at various locations on the user's body and the wearable stimulation array 200 may receive EMG signals sensed from electrodes of a different device or wearable stimulation array. For example, a user may be experiencing a limp in their right leg, wears wearable stimulation arrays on both their left and right legs, uses a first array on their left leg to measure EMG signals corresponding to a gait cycle in the left leg, and uses a second array on the right leg, which receives the measured EMG signals from the first array to stimulate electrical signals to assist in the gait cycle in the right leg.

The actuation coordination module 224 can determine a movement using IMU data to enable a corresponding actuation instruction. For example, an IMU sensor of the sensors 202 may provide kinematic signals associated with various stages of a gait cycle to the actuation coordination module 224. The module 224 may track the various stages against the predefined order of stages in a gait cycle (e.g., toe-off precedes mid-swing) to determine that a movement is likely to occur based on currently measured kinematic signals. For example, the module 224 determines that a toe-off movement is occurring using data from the IMU sensor and determines that the user is likely to perform a mid-swing movement. Based on this determination, the module 224 may apply an actuation instruction to enable the mid-swing movement. The actuation coordination module 224 may receive IMU data from the sensors 202 or a user device co-located with the user (e.g., a smartphone or smartwatch).

The actuation coordination module 224 can determine a movement using foot plantar pressure signals to enable a corresponding actuation instruction. For example, the actuation coordination module 224 may access foot plantar pressure signals from pressure sensors of the sensors 202 contacting the sole of a user's foot. The actuation coordination module 224 may use the accessed pressure signals to determine that the user is likely attempting to perform ankle plantarflexion (e.g., when jumping or standing on the tips of the toes to reach an object). In response, the module 224 may enable an actuation instruction to assist in the ankle plantarflexion. For example, the module 224 may enable actuation instructions that apply electrical stimulation via electrodes at a wearable stimulation array contacting the calve muscles to assist in the ankle plantarflexion. This wearable stimulation array contacting the calve muscles may be the same array sensing the foot plantar pressure signals or a different array that is communicatively coupled. The sensors 202 may be part of a foot pressure bed, sock, legging, or any suitable form factor for contact with the sole of the user's foot.

The actuation coordination module 224 can determine a context (e.g., when and where) to enable a corresponding actuation instruction. For example, the actuation coordination module 224 can determine contexts in which the user is likely intending to perform an ankle dorsiflexion, which may be referred to herein by "dorsiflexion" unless specified otherwise by context, such as while the user is walking, dancing, or preparing to stand from a seated position. The actuation coordination module 224 can determine a context in which the stimulated movement is to occur based on the user (e.g., user information such as body measurements, activity measurements, or the user's past or upcoming schedule), a location of the wearable stimulation array on the user's body, a time of day, or a location of the user. The actuation coordination module 224 may determine context using information stored in the user profile database 222. For example, the actuation coordination module 224 may access the user's schedule stored in the database 222 indicating that the user is scheduled to go to a dance class at 5:30 PM, determine that the time of day is 5:35 PM, and determine the context that the user is likely at a dance class and may be more likely to perform movements (e.g., knee and ankle flexions and extensions) than a context such as scheduled to be at a job at a desk where knee and ankle movement is minimal.

The actuation coordination module 224 may access a movement model (e.g., the general movement model 228 or the user-specific movement model 229) to enable actuation at the wearable stimulation array 200 (e.g., an electrical signal from one electrode to another) and stimulate movement by the user. For example, the module 224 accesses the general movement model 228 to enable actuation when a user whose movement data and actuation preferences (e.g., feedback scores for applied actuation) have not yet been recorded to provide more customized actuation. In another example, the module 224 accesses the user-specific movement model 229 to enable actuation that is more tailored to the user's body than the general movement model 228 through retraining of the model 229 using user feedback and measured stimulated movement to gauge the level of comfort or efficacy of the applied actuation instructions.

In some embodiments, the actuation coordination module 224 may stimulate the movement by enabling a first electrical signal from a first electrode to a second electrode and a second electrical signal from a third electrode to a fourth electrode. In some embodiments, a ratio of a pulse width of the first electrical signal to a pulse width of the second electrical signal is predetermined. This predetermined ratio may be referred to as a "proportional steering ratio." In one example, the actuation coordination module 224 determines a first electrode configuration where a first electrical signal of a particular frequency, pulse width, and amplitude is delivered using the electrodes in the first configuration. In this example, the actuation coordination module 224 also determines a second electrode configuration where a second electrical signal is delivered using the electrodes in the second configuration. The actuation coordination module 224 may determine pulse width of the second electrical signal using a predetermined proportional steering ratio. The ratio may be 1:4, where the pulse width of the first electrical signal is 20% and the pulse width of the second electrical signal is 80%. In this way, the actuation coordination module 224 can split the pulse width between two electrode configurations according to the proportional steering ratio. This may help increase the density of the wearable stimulation array without having to add additional physical electrodes.

The actuation coordination module 224 may determine a level of fatigue experienced by the user during movement using the measured user activity data. For example, the sensors 202 measure movement data (e.g., kinetic signals, kinematic signals, pressure signals) of the user's movement for a particular movement. The module 224 may track the amplitude of the signals of the movement data compared to a baseline signal profile of the movement. For example, during calibration, the calibration module 225 may measure and record a baseline signal profile for an ankle dorsiflexion using the IMU sensor of the sensors 202 that measures amplitude over time of the kinematic signal associated with the dorsiflexion. The module 224 may determine that the resulting dorsiflexion assisted by a particular actuation instruction is decreasing in amplitude or the duration of the movement is increasing as the user performs their daily routine due to the user's fatigue. The module 224 may determine that the amplitude has decreased by 0.5% between an earlier and later dorsiflexions or the duration has increased by 1% between the earlier and later dorsiflexions. This percentage may be proportional to a level of fatigue experienced by the user and used to adjust the actuation instruction. For example, the module 224 can access predefined levels of fatigue (e.g., a scale from 1 to 5) where a range of within ±5% variation from the baseline signal profile may correspond to the minimum level of fatigue (e.g., a level of 1), within ±25% variation from the baseline signal profile may correspond to a next higher fatigue level (e.g., level 2), within ±50%, within ±75%, and greater than ±100% variation for respective, subsequent levels.

In some embodiments, the actuation coordination module 224 may determine a level of fatigue using EMG signals measured by the sensors 202. The actuation coordination module 224 may determine a frequency response of the electroactivity in the EMG signals and determine that the frequency of electroactivity is lower (e.g., on average) than the frequency response of a baseline frequency response determined using EMG signals measured when the user was rested.

The actuation coordination module 224 may also adjust the actuation instruction (e.g., a configured power of electrical stimulation applied) based on the determined level of fatigue. Continuing the previous example, the module 224 may adjust the actuation instruction according to predefined conditions corresponding to the respective variation percentages from baseline. For example, if the kinematic signal amplitudes of a user's dorsiflexions as measured by an IMU sensor have decreased by 60% from the baseline profile, the module 224 may adjust the corresponding actuation instruction for dorsiflexion by applying a gain factor of 1.6 to the electrical stimulation applied to the user's shank.

The actuation coordination module 224 may process image or video data captured by a remote sensor (e.g., a camera communicatively coupled to the wearable stimulation array 200). For example, a user installs cameras throughout their home (e.g., as part of an assisted living or a remote care environment), where the cameras capture the user walking and transmit the captured images to the wearable stimulation array 200. The module 224 may perform image processing or apply machine learning on the captured data to recognize the position of the user's legs over time and determine a likely, upcoming movement in the user's gait cycle. The module 224 may identify each movement in a gait cycle. For example, the module 224 can determine that a terminal stance is likely to be the upcoming movement following a mid-stance identified in the latest image data received from the camera. In this way, the module 224 determines that the mid-stance depicted in the image data is a movement within the set of movements of a gait cycle.

In some embodiments, the actuation coordination module 224 determines that the user is performing a movement based on the captured image data, movement data captured from an IMU sensor or a foot pressure sensor of the sensors 202, or EMG data captured from electrodes of the electrodes 201. For example, the module 224 may weigh the output of the image processing with the output of a movement model trained to determine an actuation instruction based on movement data measured by the IMU sensor, where the model output includes an intermediate determination of the movement likely reflected in the movement data. The module 224 may weigh the output of the image processing lower than the IMU sensor, and may adjust this weight based on the user feedback. For example, if the user's feedback indicates that actuation instructions determined using IMU sensor data is unsatisfactory (e.g., causing them discomfort or is not effective in assisting with movement), the module 224 may decrease the weight of the output of the movement model or increase the weight of the output of the image processing. Alternatively or additionally, the model training engine 227 may also use this user feedback to retrain the movement model trained on IMU sensor data.

In some embodiments, the actuation coordination module 224 disables actuation. For example, the actuation coordination module 224 may receive user feedback (e.g., via a GUI at a user device communicatively coupled to the wearable stimulation array 200) to stop the actuation and the module 224 will pause or end the actuation being applied.

The calibration module 225 calibrates the actuation applied by the wearable stimulation array 200 such that it is customized to the user's body or behavior. The calibration module 225 receives user feedback of movement stimulated by the wearable stimulation array 200 and scores, using the received feedback, the corresponding actuation instruction that contributed to the stimulated movement. The scores determined by the calibration module 225 can be used by the model training engine 227 to retrain a movement model, optimizing subsequent actuation determinations with the user's feedback. Calibration can be performed periodically (e.g., once every week), on-demand, or at the initialization of the wearable stimulation array (e.g., each time the user puts on the wearable stimulation array 200).

The feedback received by the module 225 can include data measured by the sensors 202 and data provided by the user (e.g., using user interfaces through which the user can interact with the wearable stimulation array 200). User feedback through a GUI may be direct feedback (e.g., a score, star rating, thumbs up or down, etc.) or indirect feedback (e.g., adjusting the actuation or stopping the actuation) indicating a level of approval with the actuation provided by the wearable stimulation array 200. User feedback may include the efficacy of the stimulated movement as measured by the sensors 202 and compared with a neurotypical profile of the movement or the user's baseline profile of the movement. For example, the calibration module 225 may determine that the stimulated movement's measured kinematic signals are outside of a ±20% amplitude threshold with the amplitude of a neurotypical profile of the same movement and thus, determine that the stimulated movement is not effective.

In addition to using user-provided feedback to calibrate the applied stimulation, the calibration module 225 may use a target movement to evaluate the stimulated movement and retrain a movement model. The target movement may be neurotypical movement or a baseline movement set by the user. The calibration module 225 may compare the measured stimulated movement to a target movement. For example, when calibrating the wearable stimulation array 200 to help a user achieve a movement that resembles neurotypical movement, the calibration module 225 may compare the stimulated movement to neurotypical movement to determine whether an actuation instruction should be modified.

In some embodiments, the calibration module 225 may receive movement data representing a user's performance of a movement without stimulation. The calibration module 225 may determine a movement progress of the user based on the movements and retrain a movement model using the movement progress. For example, the calibration module 225 receives movement data of a user performing a knee extension once per day without stimulation helping the user. The movement data shows that the user is performing the knee extension closer and closer to the target movement over the weeks. The calibration module 225 may retrain the calibration module 225 to strengthen an association between the applied actuation instruction and the movement data associated with the knee extension.

For each actuation instruction applied during calibration, the calibration module 225 may score the resulting stimulated movement measured by a sensor (e.g., the sensors 202). The module 225 may determine the score based on one or more of received feedback (e.g., feedback directly provided by the user) or the comparison of the measured movement data with neurotypical movement data. For example, the comparison performed by the module 225 indicates that the movement stimulated on a user by the default actuation instruction for a dorsiflexion is weaker than the neurotypical movement. In response, the calibration module 225 scores the default actuation instruction low for that user (e.g., using a number system where a lower number represents poorer performance of the actuation instruction). The module 225 may store the scores in the user profile database 222.

The calibration module 225 may receive feedback from the user indicating a measure of approval of the stimulated movement in response to the use of an accessed model to stimulate a movement of a set of movements by the user using the wearable stimulation array 200. For example, after the actuation coordination module 224 uses the user-specific movement model 229 to stimulate a pre-swing in a gait cycle, the calibration module 225 receives feedback from the user indicating that the stimulation was uncomfortable (i.e., the measure of approval of the stimulated movement is low). The module 225 may calibrate the wearable stimulation array 200 by causing the model training engine 227 to retrain the accessed model to change, for at least the stimulated movement (e.g., the pre-swing) of the set of movements, a component of the actuation instruction such as an electrical signal or the electrodes that operated as anodes or cathodes.

In some embodiments, the model training engine 227 trains or retrains a movement model based on the scoring. For example, the user provides feedback that the actuation instruction caused pain where resulting electrical stimulation was applied, the module 225 scores the actuation instruction low for the corresponding movement intended to be stimulated (e.g., a knee extension), and the model training engine 227 retrains a movement model such that the likelihood of the actuation instruction being selected is decreased for subsequent determinations that the user is likely performing a knee extension.

In some embodiments, the calibration module 225 may begin calibration with a default set of actuation instructions for respective movements. The module 225 may access data representing neurotypical movements, which may be stored in the database 130, 221, or 222. The calibration module 225 compares the measured stimulated movement to a neurotypical signal profile of the corresponding movement. For example, the calibration module 225 compares measured kinetic signals of an ankle dorsiflexion to signals representing a neurotypical ankle dorsiflexion. The module 225 uses the comparison to adjust a default actuation instruction. For example, if the comparison indicates that the stimulated movement is not as strong (e.g., the amplitude of the signals are not as high) as the neurotypical movement, the module 225 may adjust the actuation instructions by changing the electrodes used to apply the electrical stimulation or the amplitude of the electrical signal. During calibration, the wearable stimulation array 200 can measure stimulated movement for various movements and compare the stimulated movement to the corresponding neurotypical data to adjust the actuation for each movement.

The calibration module 225 may adjust a frequency, an amplitude, a pulse width, or any suitable parameter of an electrical signal included within an applied actuation instruction. The calibration module 225 may also adjust the configuration of the electrodes 202, configuring the operation of an electrode to be either a cathode or an anode. These adjustments may occur sequentially such that actuation permutations are iterated through and applied for a user to determine which permutation is preferred. The calibration module 225 may apply each permutation with a pause (e.g., 10 second pause) in between consecutive actuations for a user to provide feedback of the latest actuation applied. For example, the module 225 may, as a first actuation in the iteration, enable a first electrical signal having a frequency of 20 Hz using electrode no. 1 as an anode and electrode no. 2 as a cathode. The module 225 may then pause for ten seconds to allow the user to provide feedback. The module 225 may then apply a second actuation in the iteration where the first electrical signal is applied using electrode no. 2 as an anode and electrode no. 3 as a cathode. The iterative actuations may continue through varying permutations of electrode configurations, with pauses in between each actuation, and then alter the electrical signal by incrementing the frequency by 5 Hz to produce a second electrical signal. The module 225 may then apply this second electrical signal through the same permutations of electrode configurations, pausing between each actuation to receive user feedback of the second electrical signal as applied through a particular electrode configuration. The module 225 can use the received feedback determine a score, if not directly provided by the user, and provide the determined score to the model training engine 227 to retraining the accessed model, calibrating the wearable stimulation array 200.

The calibration module 225 may adjust a signal parameter in response to user feedback. For example, the user may use a GUI shown in FIG. 5 to change the frequency or amplitude of electrical stimulation applied. When adjusting a signal parameter, the module 225 may determine indirect feedback provided by the user, as the adjustment may indirectly indicate a low measure of approval with the stimulated movement.

The calibration module 225 may store measured movement data for calibrating the wearable stimulation array 200 or training a movement model. The stored movement data characterizes movement measured by sensors on or coupled to the wearable stimulation array 200. Examples of measured movement data includes kinetic signals from IMU sensors or foot plantar pressure signals from a foot pressure bed. The calibration module 225 may also store measured motor intent data such as EMG signals measured from electrodes of the wearable stimulation array 200. The data may be stored in memory local to the array (e.g., the user profile database 222) or remote to the array (e.g., the database 130). The calibration module 225 may access the stored data to score actuation instructions for corresponding stimulated movements to calibrate the wearable stimulation array. The model training engine 227 may access the stored data to train or retrain a model (e.g., a machine learning model) to determine an actuation instruction. For example, the model training engine 227 may label the measured movement data with a corresponding actuation instruction to generate a training set to train the user-specific movement model 229.

In some embodiments, the data stored by the calibration module 225 may be used to create a movement profile of the user. For example, after the calibration module 225 has finished calibrating the wearable stimulation array 200, the kinetic signals measured when the user performs a corresponding stimulated movement or unstimulated movement may serve as a baseline signal profile of the movement when stimulated or unstimulated, respectively. These baseline profiles can be used to determine, for example, if the user is experiencing fatigue and whether the actuation coordination module 224 should adjust actuation instructions.

The GUI module 226 generates for display a GUI through which the user can provide feedback of the applied actuation instructions or control the wearable stimulation array 200. The GUI may be generated on a user device coupled to the wearable stimulation array 200. The GUI module 226 may display information describing the actuation such as properties of an applied electrical signal and through which electrodes the signal is applied (e.g., the ID numbers of the electrodes serving as the anodes and cathodes). The GUI module 226 may provide an interactive user interface that includes various buttons, toggles, menus, etc. through which a user can adjust the applied actuation (e.g., as depicted in FIG. 5). The interactive user interface may also include user inputs for providing feedback (e.g., as depicted in FIG. 6).

The model training engine 227 may train a machine learning model in multiple stages. In a first stage, the model training engine 227 may use generalized data representative of measured movement (e.g., kinetic signals, kinematic signals, or EMG signals) collected across one or more users (e.g., a neurotypical population) to train the machine learning model. The model training engine 227 may label the generalized data with an instruction label representative of the actuation instruction that should be applied to assist with the measured movement represented by the generalized data. The model training engine 227 creates a first training set based on the labeled generalized data. The model training engine 227 trains a machine learning model (e.g., the general movement model 228), using the first training set, to determine an actuation instruction to enable using the wearable stimulation array 200. That is, the machine learning model is configured to receive, as an input, measured movement data (e.g., from the sensors 202) or measured motor intent data (e.g., from the electrodes 201), and output the actuation instruction corresponding to the likely motion characterized by the measured data.

In a second stage of training, the model training engine 227 can use user-specific data collected by the sensors 202 or the electrodes 201 measuring movement by the user wearing the wearable stimulation array 200. The model training engine 227 creates a second training set based on previously determined actuation instructions (e.g., by the trained general movement model 228) and the data representative of measured movement collected from the user of wearable stimulation array 200 (i.e., user-specific data). The determined actuation instructions, depending on the success of the corresponding applied actuation (e.g., as indicated by user feedback), may serve as labels for the user-specific data. If a previously determined actuation instruction resulted in stimulated movement that was effective or comfortable, the model training engine 227 may create the second training set that includes user-specific data labeled with the determined actuation instruction. The model training engine 227 then re-trains the machine learning model using the second training set such that the machine learning model is customized to the user's motions. For example, the model training engine 227 may re-train the general movement model 228 such that the re-trained model is the user-specific movement model 229.

To create a training set, the model training engine 227 may determine one or more feature vectors associated with measured movement data (e.g., a combination of kinetic signals from different muscles and the timing of their firing during the measured movement). For example, the model training engine 227 may determine a feature vector characterizing muscle firing events associated with a certain degree of knee flexion and a toe off event during a gait cycle. In some embodiments, the model training engine 227 may receive calibration data (e.g., from the calibration module 225) associated with calibration performed prior to stimulating movement. The model training engine 227 may use the calibration data in creating the training set such that the trained machine-learned model is further customized to the user's motions.

The general movement model 228 is configured to enable, for each of various movements, a corresponding actuation. For example, for each movement in a gait cycle, the general movement model 228 can determine a corresponding electrical signal to drive from a first electrode or first set of electrodes of the electrodes 201 to a second electrode or second set of electrodes of the electrodes 201. The general movement model 228 receives, as input, data representing the movement measured by the wearable stimulation array 200 and outputs an actuation instruction to assist with the movement that is likely represented in the received data. The data representing the measured movement may include EMG data, IMU data, foot plantar pressure signals, a level of fatigue of the measured movement, a context in which the stimulated movement is to occur, any suitable activity data, or combination thereof. In one example, a set of the electrodes of the electrodes 201 are configured to sense EMG signals at the shank (e.g., sensed when the user is intended to perform an ankle dorsiflexion), the EMG signals are input into the general movement model 228, and the general movement model 228 outputs an actuation instruction to stimulate an ankle dorsiflexion. The general movement model 228 is trained by the model training engine 227 using movement data, or any other suitable data representing measured movement, collected across a neurotypical population performing a variety of general movements. The general movements may include walking, standing (i.e., from a sitting position), sitting, ascending or descending steps, grasping, any suitable movement used in day-to-day activity, or a combination thereof.

The user-specific model 229 is trained by the model training engine 227 using movement data, or any other suitable data representing measured movement, collected from the sensors 202 or the electrodes 201. The model 229 may be obtained by re-training the general movement model 228. Because the model 229 may be trained on user-specific movement data, the model 229 enables the mobility augmentation system 220 to be personalized to the user and improve its accuracy in identifying actuation instructions that the user finds satisfactory (e.g., effective or comfortable). The user-specific model 229 may, similar to the general movement model 228, be configured to enable, for each of various movements, a corresponding actuation instruction.

The general movement model 228 and user-specific movement model 229 may be machine learning models. Machine learning models of the mobility augmentation system 220 may use various machine learning techniques such as linear support vector machine (linear SVM), boosting for other algorithms (e.g., AdaBoost), neural networks, logistic regression, naïve Bayes, memory-based learning, random forests, bagged trees, decision trees, boosted trees, boosted stumps, a supervised or unsupervised learning algorithm, or any suitable combination thereof. The machine learning models may have access to a broader set of features on which to train. The models may use physiological simulation as a component for determining an actuation instruction.

Alternatively, the models described herein may be a statistical model generated based on previously measured movement data and corresponding actuation applied, the statistical model configured to determine an actuation that is most likely to correspond to measured movement data. The models described herein may also be a rules-based decision model that determines an optimal actuation based on a test of various rules or conditions such as whether the measured movement data deviates from target data by over a threshold, whether the user has been wearing the array for longer than a predetermined period of time, or any other suitable test for determining conditions under which a particular actuation should be applied.

Although the mobility augmentation system 220 is depicted as being a component of the wearable stimulation array 200, the remote mobility augmentation system 120 may provide the same or similar functionality such that the processing burden is shifted from the MCU 204 to processors local to the remote server hosting the remote mobility augmentation system 120. The data captured by the sensors 202 or EMG signals captured electrodes of the electrodes 201 may be communicated via the communications circuitry 206 to the remote mobility augmentation system 120. For example, kinetic movement data measured by the IMU sensors of the sensors 202 are stored in a Secure Digital (SD) memory card at the wearable stimulation array 200, the mobility augmentation system 220 uploads data from the SD card to a remote database (e.g., the database 130), and the remote mobility augmentation system 120 accesses the database 130 to calibrate a movement model that is accessed over the network 160 by the wearable stimulation array 200. The remote mobility augmentation system 120 may be hosted on a computing device such as a smartphone or a tablet, where the computing device can be communicatively coupled to the wearable stimulation array 200 via a communication network (e.g., the network 150).

The power source 205 provides electrical power for the wearable stimulation array 200 to operate. The power source 205 may be a mobile power source such as a battery or a fixed power source such as an outlet connection to power. The power source 205 may provide power for actuation that includes electrical stimulation via the electrodes 202. For example, the actuation coordination module 224 may activate or deactivate an electrical connection between the power source 205 and the electrodes 201 to control electrical stimulation. The power source 205 may provide power for actuation that includes mechanical stimulation via, although not depicted in FIG. 2, a vibrating motor in the wearable stimulation array 200. For example, the actuation coordination module 224 may activate or deactivate an electrical connection between the power source 205 and the vibrating motor to provide haptic or mechanical actuation.

The communications circuitry 206 enables the wearable stimulation array 200 to communicate over a network (e.g., the network 160). The communications circuitry 206 may be configured to establish a connection between the wearable stimulation array 200 and the Internet using one or more of a Wi-Fi, cellular, local area network (LAN) interface, or any suitable interface for wireless communication. The communications circuitry 206 may be configured to transmit and receive data from communications circuitry of other devices (e.g., other wearable stimulation arrays or a user device). In some embodiments, the communications circuitry 206 may also enable wired communication through various mediums such as fiber-optic, USB, serial, coaxial, or any suitable cable for wired networking.

Figure 3:
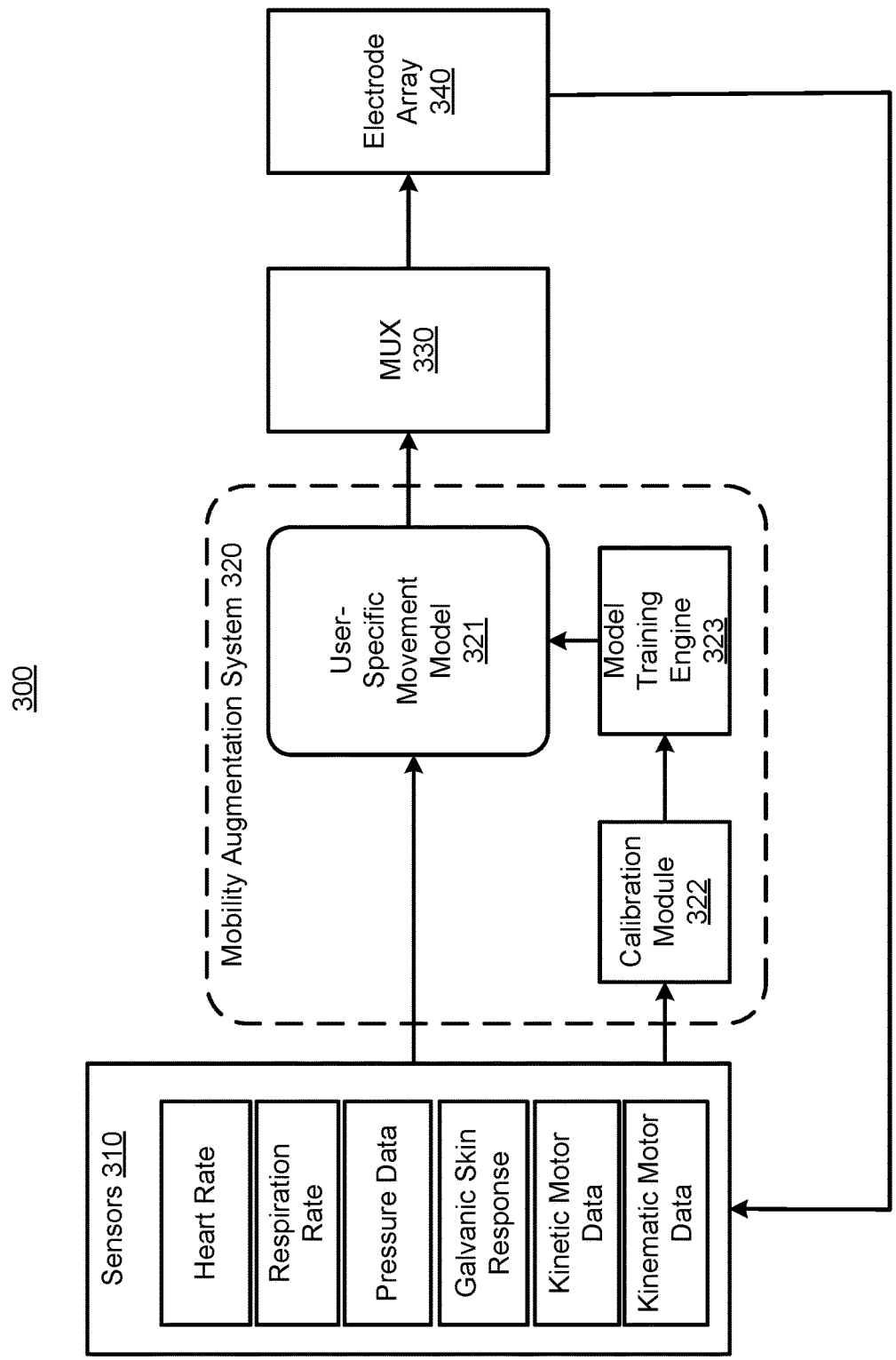
FIG. 3 is a block diagram of a feedback loop for optimizing stimulation by the wearable stimulation array, in accordance with at least one embodiment.

FIG. 3 is a block diagram of a feedback loop 300 for optimizing stimulation by the wearable stimulation array, in accordance with at least one embodiment. The feedback loop 300 is a closed-loop system that minimizes differences between a movement stimulated by a wearable stimulation array and a target movement (e.g., neurotypical movement). The mobility augmentation system 220 may perform the feedback loop 300. The feedback loop 300 includes sensors 310, a mobility augmentation system 320, a MUX 330, and an electrode array 340. The mobility augmentation system 320 executes a user-specific movement model 321, a calibration module 322, and a model training engine 323. The feedback loop 300 may have alternative configurations than shown in FIG. 3, including for example different, fewer, or additional components.

The optimization of stimulated movement begins with an initial application of actuation. The sensors 310 measure movement data such as a user's heart rate, respiration rate, pressure data (e.g., using pressure beds at the user's feet), galvanic skin response, kinetic movement data, kinematic movement data, or any combination thereof. The sensors 310 function similarly to the sensors 202. The sensors 310 provide the movement data to the mobility augmentation system 320, which determines an actuation instruction to apply using the user-specific movement model 321. The system 320 may be similar to the mobility augmentation system 220 described in FIG. 2 (e.g., the model 321 may function similarly to the user-specific movement model 229). The determined actuation instructions can specify a combination of electrodes to activate. The mobility augmentation system 320 uses the MUX 330 to select the specified combination (i.e., by outputting selection signal values corresponding to the specified combination). The MUX 330 functions similarly to the MUX 203. The MUX 330 enables the specified combination of electrodes in the electrode array 340 to provide electrical stimulation to the user.

The feedback needed for optimization is obtained when the sensors 310 measure the movement data representing the stimulated movement. This measurement is depicted in FIG. 3 by the arrow from the electrode array 340 to the sensors 310. Examples of feedback indicating that the level of approval of the stimulated movement is low includes measures of the body's routine functions (e.g., heart rate, respiration rate, galvanic skin response) that are outside of a normal range of values for the user (e.g., according to the user's age or height). Other examples of feedback indicating that the level of approval of the stimulated movement is low includes a comparison of the measured kinetic movement data, kinematic movement data, or pressure data against a respective set of target data that deviates beyond a predetermined threshold. For example, the level of approval of the stimulated movement may be low when the measured kinetic signals of a dorsiflexion deviate from signals of a target dorsiflexion (e.g., a dorsiflexion performed by the user during calibration or a neurotypical dorsiflexion) by ±25% of the target dorsiflexion's amplitude.

Examples of feedback indicating that the level of approval of the stimulated movement is high includes measures of the body's routine functions that are within of a normal range of values for the user. Other examples of feedback indicating that the level of approval of the stimulated movement is high includes a comparison of the measured kinetic movement data, kinematic movement data, or pressure data against a respective set of target data that meets or falls within a predetermined threshold. For example, the level of approval of the stimulated movement may be high when the amplitude of measured pressure signals from a heel strike fall within ±10% of the target heel strike's amplitude.

The feedback is used to retrain the user-specific movement model 321. The measured movement data from the sensors 310 is provided to the calibration module 322. The calibration module 322 may score the applied actuation instruction based on the level of approval of the stimulated movement, which may be determined by the mobility augmentation system 320. The level of approval may be proportional to an amount by which the stimulated movement deviates from a target movement, and the score may be proportional to the level of approval. Using the score, the model training engine 323 may create a training set of labeled data. Movement data can be labeled with an actuation instruction depending on the determined score. For example, if the score of the stimulated movement is low due to low level of approval, the model training engine 323 may create a negative sample using the applied actuation as a label to the measured movement that resulted in the unsatisfactory actuation to be applied. In another example, if the score of the stimulated movement is high due to a high level of approval, the model training engine 323 may similarly create a positive sample. The model training engine 323 can use the positive and negative samples to re-train the user-specific movement model 321 to refine the applied stimulation based on the user's body and behavior.

Figure 4:
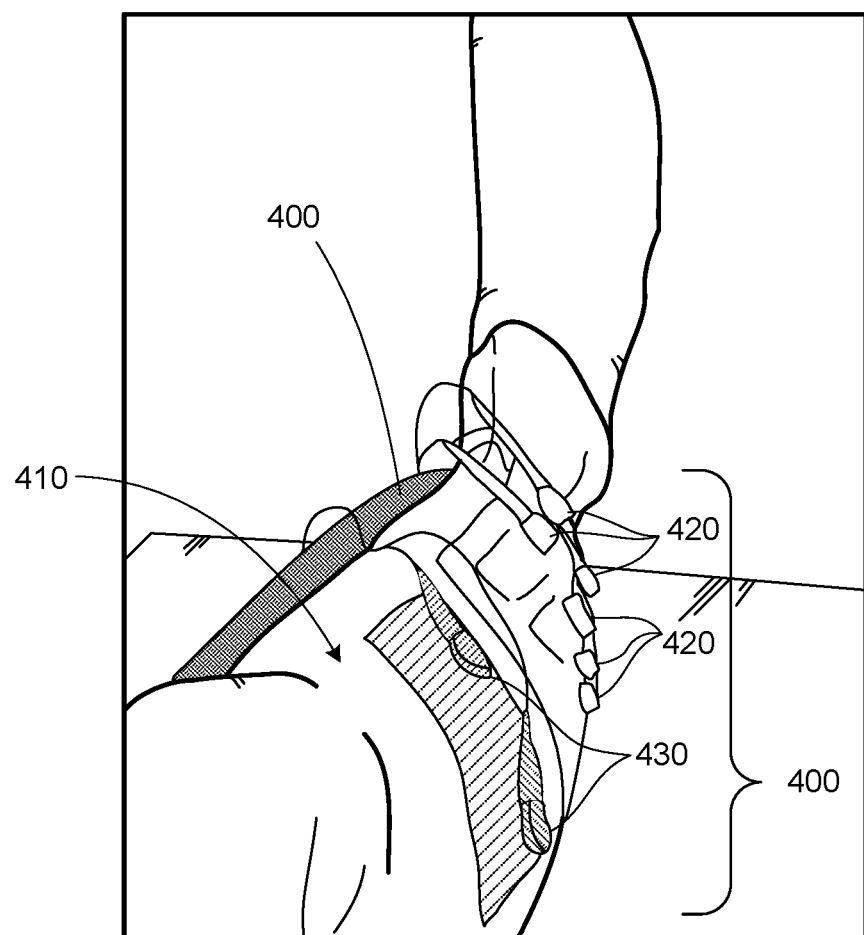
FIG. 4 depicts electrodes of a wearable stimulation array in contact with a user's shank, in accordance with at least one embodiment.

FIG. 4 depicts electrodes of a wearable stimulation array 400 in contact with a user's shank 410, in accordance with at least one embodiment. The wearable stimulation array 400 is depicted without integration into an article of clothing such as a legging or sock. The wearable stimulation array 400 includes components of the wearable stimulation array 200 such as electrodes 420 and 430. The electrodes 420 may be configured as anodes and the electrodes 430 may be configured as cathodes. The wearable stimulation array 400 depicted is an 8-electrode array having two cathodes and six anodes.

In some embodiments, a first set of the electrodes of the wearable stimulation array 400 may be configured to be electrodes for an EMG sensor of the array 400. For example, a MUX of the array 400 may select two electrodes of the 8-electrode array to be coupled to the EMG sensor. The movement data (e.g., EMG signals) sensed by the two electrodes may be applied to a movement model executed on the MCU of the array 400. The accessed movement model may output an actuation instruction determined as most optimal to stimulate the movement represented in the EMG signals. The determined actuation instruction may specify how the remaining six electrodes of the 8-electrode array may be configured (e.g., anode or cathode) and one or more electrical signals to be applied through the electrodes. The determined actuation instruction may alternatively specify that the two electrodes used for the EMG sensor be reconfigured to apply the actuation (i.e., the electrodes' roles are reconfigured from being EMG electrodes to either a cathode or anode for the electrical stimulation) to the shank 410. Disconnecting the electrodes from the EMG sensor and reconfiguring the disconnected electrodes for use in electrical stimulation may help EMG measurements avoid or reduce interference from the electrical stimulation (e.g., from the electrode MUX used to apply the stimulation).

Graphical User Interfaces for Mobility Augmentation

FIG. 5 depicts graphical user interfaces (GUIs) 500a and 500b for managing electrical stimulation by a wearable stimulation array, in accordance with at least one embodiment. The GUIs 500a-b may be displayed on a user device (e.g., the user device 150). The GUI module 226 of the wearable stimulation array 200 may provide the actuation information for display at the GUIs 500a-b. The GUIs 500a-b include a heading 510, a table 520, and indicators 530. The GUIs 500a-b show two different actuation configurations for electrical stimulation applied via electrodes of the wearable stimulation array 200. In particular, the electrical signal of the stimulation is equivalent but the roles of the electrodes, as shown by the indicators 530, is different. A first set of electrodes is displayed in the GUI 500a as operating as anodes and a second set of electrodes is displayed in the GUI 500b as operating as anodes. One electrode is shown as operating as a cathode in both the GUIs 500a-b. The indicators 530 that are not shaded may reflect electrodes that are inactive (i.e., not used to provide electrical stimulation).

The GUIs 500a-b include an actuation location heading 510 to indicate where the actuation is applied. The heading 510 may be user specified. For example, when the user first initializes the wearable stimulation array 200, the user may place the electrodes 201 in contact with the left tibialis anterior and specify, via the GUIs 500a-b, where the array 200 is located. The left tibialis anterior is shown as an example of where electrodes of a wearable stimulation array can be placed, and those skilled in the art will recognize that electrical stimulation may be applied to other locations on the human body.

The GUIs 500a-b include a table of electrical signal parameters 520 and indicators 530 representing the configuration of the array's electrodes. The table 520 and the indicators 530 may be interactive, enabling the user to adjust the signal parameters shown in the table 520 or reconfigure the roles of the electrodes by selecting the indicators 530. For example, the user may be able to select a frequency, duration, or amplitude of the electrical stimulation by swiping a touch screen of the user device 150 displaying the GUIs 500a-b. The indicators 530 may be colored using at least 3 different colors representing an inactive electrode, active electrode configured as an anode, and an active electrode configured as a cathode. Additionally colors (or any suitable graphical distinction), although not shown, may be used to indicate additional roles of the electrodes (e.g., indicating an EMG electrode). In one example, a user may adjust the roles of the electrode by selecting (e.g., tapping on a touch screen of the device 150) a button, where each selection changes the color of the button and in parallel, the corresponding role of the electrode.

FIG. 6 depicts GUIs 600a and 600b for providing feedback of stimulated movement provided by a wearable stimulation array, in accordance with at least one embodiment. The GUIs 600a-b show two different interfaces for providing feedback. The GUIs 600a-b may be displayed on a user device (e.g., the user device 150). The GUI module 226 of the mobility augmentation system 220 may provide the information for display at the user device 150. Both interfaces enable the user to indicate a level of approval of actuation applied by, for example, the wearable stimulation array 200. As described in the description of the calibration module 225, the user can indicate the level of approval using direct feedback via evaluation on a scale (e.g., a numerical score, star rating, etc.) or a binary rating (e.g., a thumbs up or down). The user can also provide indirect feedback through adjustments of actuation or selection of a preferred actuation. The mobility augmentation system 220 can use the indirect feedback to generate a score for the actuation instruction (i.e., as opposed to directly using a score provided by the user).

The GUI 600a includes a heading 610, actuation information window 620, and feedback buttons 630. The heading 610, similar to the heading 510, indicates the muscle or muscle group to which the actuation is applied. As shown in the GUIs 600a-b, the heading 510 indicates that the actuation is applied to the left tibialis anterior. The actuation information window 620 displays information regarding the actuation applied to the left tibialis anterior. In particular, the window 620 shows information regarding applied electrical stimulation: the frequency, duration, and amplitude of the electrical signal and the electrode configuration used to deliver the electrical signal. The user can interact with the feedback buttons 630 to indicate whether the applied electrical stimulation indicated in the window 620 is satisfactory (e.g., comfortable or effective for stimulating a particular movement). For example, the user may tap a touch screen of the user device 150 to select a thumbs up of the buttons 630 to indicate that the applied stimulation is comfortable or effective.

The GUI 600b includes the heading 610, actuation information windows 640, and actuation selection buttons 650. The actuation information windows 640 display a side-by-side comparison of two actuation instructions from which the user may select. The mobility augmentation system 220 may provide the GUI 600b for display while cycling through various actuation instructions during calibration. For example, the calibration module 225 may adjust the actuation in a predetermined sequence (e.g., stepping up or down the amplitude of the signal by 10% of the maximum amplitude every 10 seconds), display two consecutive actuations on the GUI 600b, and enable the user to select which of the two actuations the user prefers. The mobility augmentation system 220 may enable the two actuation information windows 640 to be interactive. For example, the user can tap either of the windows 640 to cause the wearable stimulation array 200 to execute the actuation (i.e., in response to detecting the user has selected either of the windows 640, the actuation coordination module 224 may enable the corresponding actuation). This interaction and on-demand actuation calibration can help the user determine a preferred actuation. The user can interact with the feedback buttons 630 to indicate which of the applied electrical stimulations presented in the windows 640 is satisfactory. The interactions between the user and the GUIs 600a-b can be stored in the user profile database 222 to maintain a record of the user's preferences.

Alternatively or additionally, the GUIs shown in FIGS. 5-6 can be displayed at a display of a wearable stimulation array. Although not depicted in FIG. 2, the wearable stimulation array 200 may include user inputs and outputs such as a display screen, buttons to interact with what is displayed, a touch-screen display, a microphone and speaker (e.g., for voice control of the wearable stimulation array 200 when the MCU 204 is configured with natural language processing software), any suitable visual, audio, or tactile mechanism for enabling communication between the array and the user, or a combination thereof. In this way, a wearable stimulation array may be configured to receive feedback from a user without an additional device or when the array is offline (e.g., unable to communicate with the user device 150 to receive user feedback).

Figure 7:
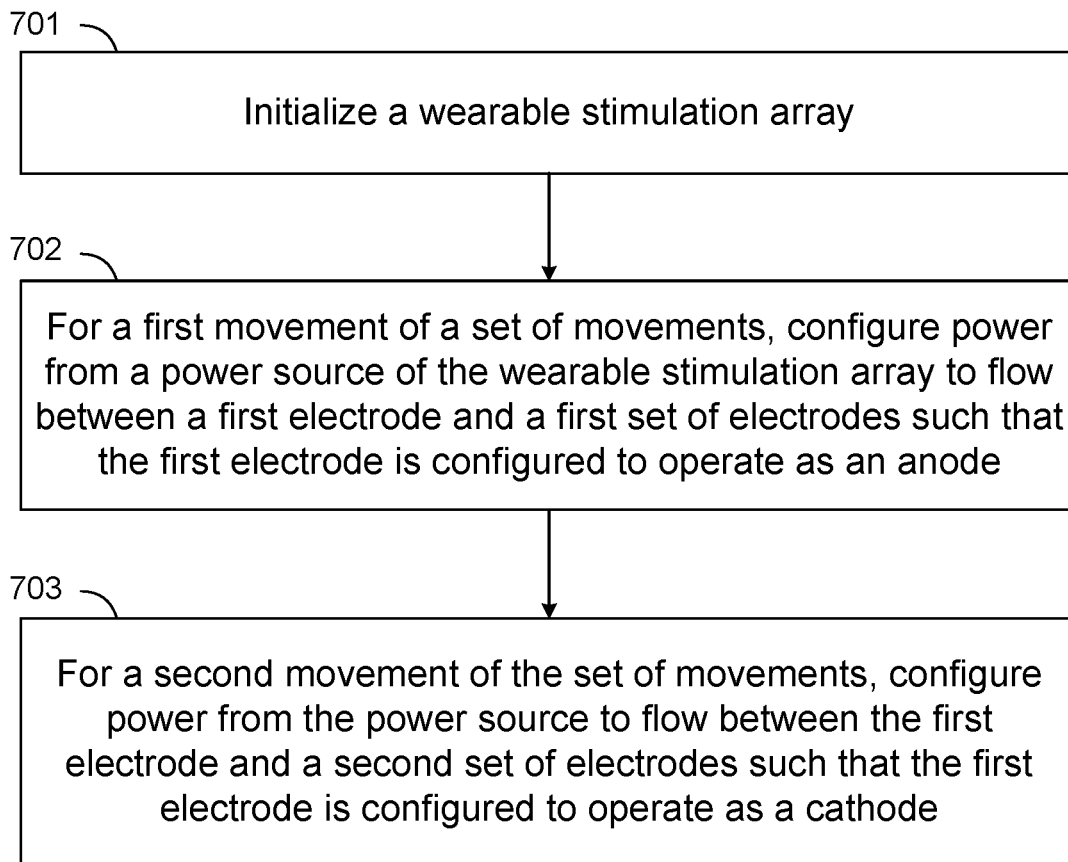
FIG. 7 is a flowchart illustrating a process for enabling movement stimulation by a wearable stimulation array, in accordance with at least one embodiment.

Processes for Calibrating and Applying Actuation in Mobility Augmentation Systems FIG. 7 is a flowchart illustrating a process 700 for enabling movement stimulation by a wearable stimulation array, in accordance with at least one embodiment. In some embodiments, the mobility augmentation system 220 performs operations of the process 700 in parallel or in different orders, or performs different steps.

The mobility augmentation system 220 initializes 701 a wearable stimulation array (e.g., the wearable stimulation array 200). The initialization module 223 of the mobility augmentation system 220 may initialize 701 the array 200 by beginning to measure movement data (e.g., using the sensors 202) in response to detecting that the user is wearing the array 200. The initialization module 223 may determine if the user is wearing the array 200 using the sensors 202. For example, a heart rate sensor of the sensors 202 may detect the user's heart rate and thus, the initialization module 223 determines that the user is wearing the array 200. In some embodiments, the wearable stimulation array 200 may include a user interface (e.g., a switch) for manually initializing 701 the array 200.

The mobility augmentation system 220 configures 702, for a first movement of a set of movements, power from a power source of the wearable stimulation array to flow between a first electrode and a first set of electrodes such that the first electrode is configured to operate as an anode. For example, the wearable stimulation array 200 may be configured to stimulate a set of movements including sit-to-stand movements such as knee flexion and ankle dorsiflexion. The actuation coordination module 224 may use the MUX 203 to configure 702, for a knee flexion of the sit-to-stand movements, power from the power source 205 to flow between electrode ID no. 1 of the electrodes 201 and electrodes ID nos. 2-4 such that electrode no. 1 is an anode, where current flows from electrode nos. 2-4 to the user to stimulate the knee flexion and is received by electrode no. 1 to complete the flow. The actuation coordination module 224 may use a machine learning model (e.g., the user-specific movement model 229) to determine the actuation instruction that is most likely to stimulate the knee flexion. The determined actuation instruction may specify a combination of selection signals that can be input to the MUX 203 for enabling electrode no. 1 to operate as an anode and electrode nos. 2-4 to be cathodes.

The mobility augmentation system 220 configures 703, for a second movement of the set of movements, power from the power source of the wearable stimulation array to flow between the first electrode and a second set of electrodes such that the first electrode is configured to operate as an cathode. Continuing the previous example, the actuation coordination module 224 may use the MUX 203 to configure 703, for an ankle dorsiflexion of the sit-to-stand movements, power from the power source 205 to flow between electrode ID no. 1 of the electrodes 201 and electrode ID no. 8 such that electrode no. 1 is a cathode, where current flows from electrode no. 1 to the user to stimulate the dorsiflexion and is received by electrode no. 8 to complete the flow. The actuation coordination module 224 may use the user-specific movement model 229 to determine the actuation instruction that is most likely to stimulate the ankle dorsiflexion. The determined actuation instruction may specify a combination of selection signals that can be input to the MUX 203 for enabling electrode no. 1 to operate as a cathode and electrode no. 8 to operate as an anode.

Figure 8:
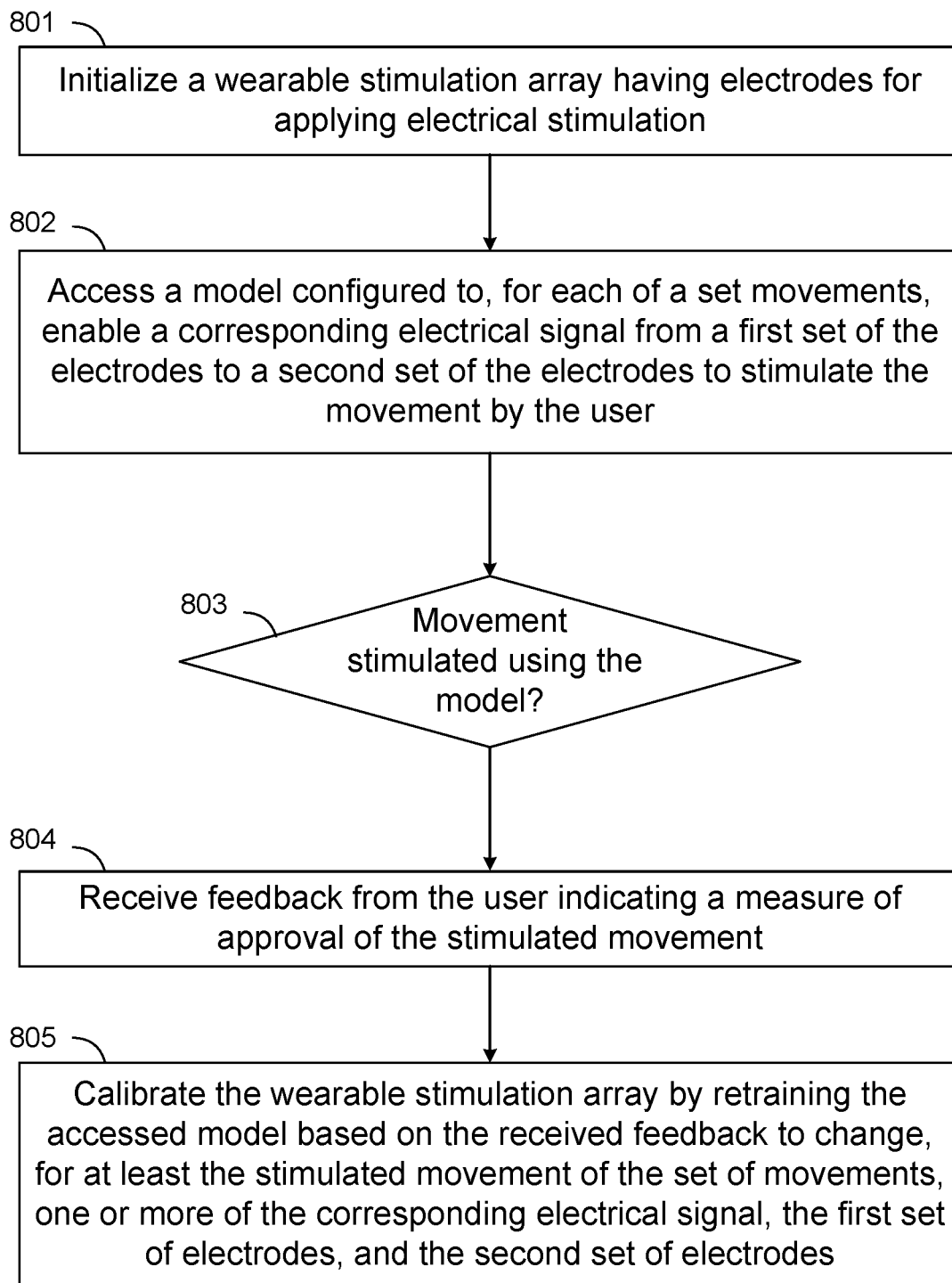
FIG. 8 is a flowchart illustrating a process for calibrating a wearable stimulation array, in accordance with at least one embodiment.

FIG. 8 is flowchart illustrating a process 800 for calibrating a wearable stimulation array, in accordance with at least one embodiment. In some embodiments, the mobility augmentation system 220 performs operations of the process 800 in parallel or in different orders, or may perform different steps. For example, the calibration shown in process 800 may be a feedback loop with an additional arrow back from calibrating 805 the wearable stimulation array to accessing 802 the model to determine an electrical stimulation to apply. A decision block may also be added between calibrating 805 the array and accessing 802 the model, where the process 800 returns to access 802 the model if the received 804 feedback indicated a low measure of approval with the movement stimulated using the model.

The mobility augmentation system 220 initializes 801 a wearable stimulation array including electrodes. Similar to the initializing 701 of the process 700, the initializing 801 of the process 800 may be performed by the initialization module 223 of the mobility augmentation system 220. The module 223 may initialize the array 200 by beginning to measure movement data (e.g., using the sensors 202) in response to detecting that the user is wearing the array 200. The initialization module 223 may determine if the user is wearing the array 200 using the sensors 202. For example, a heart rate sensor of the sensors 202 may detect the user's heart rate and thus, the initialization module 223 determines that the user is wearing the array 200. In some embodiments, the wearable stimulation array 200 may include a user interface (e.g., a switch) for manually initializing 801 the array 200.

The mobility augmentation system 220 accesses 802 a model configured to, for each of various movements, enable a corresponding electrical signal from a first set of the electrodes (i.e., electrodes operating as cathodes) to a second set of the electrodes (i.e., electrodes operating as anodes) to stimulate the movement by the user. The mobility augmentation system 220 may determine actuation instructions to stimulate a variety of movements such as the movements within a gait cycle. For example, the actuation coordination module 224 can access 802 a machine learning model (e.g., the general movement model 228) that is configured to, for movements within a gait cycle such as a toe-off and mid-swing, enable a corresponding actuation (e.g., electrical signal) from a first set of the electrodes 201 to a second set of the electrodes 201 to stimulate a movement (e.g., the toe-off) by the user. The system 220 accesses 802 the general movement model 228 by applying the model 228 to movement data measured by the sensors 202. For example, the actuation coordination module 224 receives kinetic movement data from IMUS at a shank or foot of the user. The module 224 then applies the received kinetic movement data to the general movement model 228, which outputs an actuation instruction that is likely to assist with the toe-off.

The mobility augmentation system 220 determines 803 whether a movement has been stimulated using the model. Continuing the previous example, the actuation coordination module 224 may enable the electrodes 201 to provide electrical stimulation to the user's leg to assist with a toe-off after determining the corresponding actuation instruction specifying how the electrical stimulation should be applied. The calibration module 225 may determine 803 that the toe-off has been stimulated using the model (i.e., via the actuation instruction determined by the model) using the output from the sensors 202. For example, data from an IMU or a foot pressure bed of the sensors 202 may indicate that the user has activated muscles at the location where the electrical stimulation was applied.

The mobility augmentation system 220 receives 804, in response to the use of the accessed model to stimulate a movement of the various movements by the user using the wearable stimulation array, feedback from the user indicating a measure of approval of the stimulated movement. For example, the calibration module 225 receives 804 feedback from the user indicating that the stimulation was comfortable. The user may use an interface such as the GUI 600a shown in FIG. 6 to provide direct feedback of the stimulated movement (e.g., using a thumbs up). Alternatively, the lack of feedback may provide indirect feedback that the user was satisfied with the stimulation. For example, the calibration module 225 may wait one minute after determining 803 that the movement was stimulated using the model and not receive any feedback from the user (i.e., receiving 804 indirect feedback). These examples of direct and indirect feedback from the user can indicate a high measure of approval.

In another example, the calibration module 225 receives 804 feedback from the user indicating that the stimulation was ineffective in helping with the toe-off using a thumbs down in the GUI 600a. The calibration module 225 may receive 804 indirect feedback that the stimulation was ineffective by receiving 804 a request from the user to adjust the electrical stimulation (e.g., selecting a different stimulation among the options in the actuation information windows 640). These examples of direct and indirect feedback from the user can indicate a low measure of approval.

The mobility augmentation system 220 calibrates 805 the wearable stimulation array by retraining the accessed model based on the received feedback to change, for at least the stimulated movement of the various movements, one or more of the corresponding electrical signal, the first set of electrodes, and the second set of electrodes. For example, the model training engine 227 may retrain the general movement model 228 using the feedback for the stimulated toe-off that was received 804 from the user. If the feedback received 804 indicates a high measure of approval, the model training engine 227 may generate a training set that includes a positive sample of the movement data previously input into the general movement model 228 labeled with the determined actuation. Alternatively, if the feedback received 804 indicates a low measure of approval, the model training engine 227 may generate a training set that includes a negative sample of the movement data labeled with the determined actuation. The model training engine 227 may use the generated training set to retrain the general movement model 228.

The output of the retrained model 228 may change the determined actuation instruction chosen to stimulate subsequent toe-offs performed by the user. The output of the retrained model 228 may include a different electrical signal (e.g., a different frequency of the previously applied signal), a different electrode designated to operate as a cathode, or a different electrode designated to operate as an anode. This change in actuation, which may continue changing until the user provides feedback indicating a high measure of approval of the applied stimulation, contributes to the calibration 805 of the wearable stimulation array 200.

Additional Considerations

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm may be a sequence of operations leading to a desired result. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

It should be borne in mind, however, that all of these and similar terms are to be associated with the appropriate physical quantities and are merely convenient labels applied to these quantities. Unless specifically stated otherwise as apparent from the present disclosure, it is appreciated that throughout the description, certain terms refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may include a computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various other systems may be used with programs in accordance with the teachings herein, or it may prove convenient to construct a more specialized apparatus to perform the method. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment. Where values are described as "approximate" or "substantially" (or their derivatives), such values should be construed as accurate +/−10% unless another meaning is apparent from the context. From example, "approximately ten" should be understood to mean "in a range from nine to eleven."

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present). In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A wearable stimulation array comprising:
   a set of configurable electrodes each configured to contact a different portion of a surface of a body of a user when the wearable stimulation array is worn by the user;
   a power source;
   a memory storing a machine-learned movement model trained using measured movement data associated with respective actuation instructions, the movement model configured to determine actuation instructions likely to stimulate a set of movements, each actuation instruction specifying an electrical signal to be transmitted from a given electrode to a different electrode; and
   a controller coupled to the set of configurable electrodes, the memory, and the power source, the controller configured to:
      stimulate a first movement of the set of movements by configuring current from the power source to flow in a direction between a first electrode and a first set of electrodes such that the first electrode is configured to operate as an anode; and
      stimulate a second movement of the set of movements by configuring the current to flow in a different direction between the first electrode and a second set of electrodes such that the first electrode is configured to operate as a cathode.

2. The wearable stimulation array of claim 1, wherein the controller is further configured to determine each movement of the set of movements based on one or more of electromyography (EMG) data, inertial measurement unit (IMU) data, foot plantar pressure signals, or a context in which the movement occurs.

3. The wearable stimulation array of claim 1, wherein one or more electrodes of the set of configurable electrodes are configured to alternate between providing stimulation and measuring EMG data.

4. The wearable stimulation array of claim 1, wherein a movement of the set of movements represents a phase of a gait cycle.

5. The wearable stimulation array of claim 1, wherein the wearable stimulation array further comprises a plurality of sensors including one or more of a heart rate sensor, IMU sensor, or pressure sensor coupled to the controller.

6. The wearable stimulation array of claim 5, wherein the controller is further configured to:
   receive measurements taken from the plurality of sensors; and
   detect that the user is wearing the wearable stimulation array using the received measurements.

7. The wearable stimulation array of claim 5, wherein the controller is further configured to:
   measure user activity data including one or more of galvanic skin response, heart rate, or respiration rate using the plurality of sensors;
   determine a level of fatigue experienced by the user during movement using the measured user activity data; and
   adjust the configured current based on the level of fatigue.

8. The wearable stimulation array of claim 1, wherein the wearable stimulation array further comprises one or more of an IMU sensor or a foot pressure sensor and wherein the controller is further configured to:
   measure a movement using the IMU sensor or the foot pressure sensor; and
   store data characterizing the measured movement, wherein the stored data is applied to the movement model to stimulate movement or used to characterize a movement profile of the user.

9. The wearable stimulation array of claim 1, wherein the wearable stimulation array further comprises one or more of an IMU sensor or a foot pressure sensor and wherein the controller is further configured to:
   measure a movement stimulated by the wearable stimulation array, the movement measured using one or more of the IMU sensor or the foot pressure sensor;
   compare the measured stimulated movement to a predetermined movement representative of neurotypical movement;
   score the measured movement based on the comparison; and
   retrain the machine-learned movement model based on the scoring.

10. The wearable stimulation array of claim 1, wherein the controller is further configured to:
    create a training set comprising the measured movement data associated with the respective actuation instructions; and
    train the machine-learned movement model using the training set.

11. The wearable stimulation array of claim 10, wherein the controller is further configured to retrain the machine-learned movement model by:
    receiving feedback from the user indicating a measure of approval of a movement stimulated by the wearable stimulation array;

in response to the received feedback indicating the measure of approval of the stimulated movement is high, strengthening an association between the stimulated movement and an actuation instruction comprising enabling an electrical signal from a first electrode to a second electrode; and in response to the received feedback indicating the measure of approval of the stimulated movement is low, weakening an association between the stimulated movement and the actuation instruction.

12. The wearable stimulation array of claim 1, wherein the controller is further configured to:

stimulate a third movement of the set of movements by:
generating a first electrical signal from the first electrode to the second electrode, and
generating a second electrical signal from a third electrode to a fourth electrode, wherein a ratio of a pulse width of the first electrical signal to a pulse width of the second electrical signal is predetermined.

13. The wearable stimulation array of claim 1, wherein the controller is further configured to:

provide for display at a graphical user interface (GUI) information describing one or more of the configured current, the first set of electrodes, or the second set of electrodes;
receive a user selection of an electrode of the set of configurable electrodes to enable; and
in response to receiving the user selection:
change one or more of the first set of electrodes or the second set of electrodes to include the user-selected electrode, and
retrain the machine-learned movement model based on the user selection.

14. The wearable stimulation array of claim 1, further comprising a camera coupled to the controller, the camera configured to:

capture an image depicting movement by the user; and
provide the captured image to the controller, wherein the controller is further configured to determine that the depicted movement is a movement within the set of movements.

15. The wearable stimulation array of claim 14, wherein the controller is further configured to determine that the user is performing the movement based on the captured image and movement data captured from an IM sensor or a foot pressure sensor coupled to the wearable stimulation array.

16. The wearable stimulation array of claim 1, wherein the wearable stimulation array is coupled to a legging such that the set of configurable electrodes contacts a leg of the user.

17. The wearable stimulation array of claim 1, wherein the wearable stimulation array is coupled to a sock or a shoe insole such that the set of configurable electrodes contacts a foot of the user.

18. The wearable stimulation array of claim 1, wherein the controller is further configured to:

receive, from one or more sensors of a plurality of sensors of the wearable stimulation array, kinematic signals associated with the set of movements; and
determine, using the kinematic signals and the movement model, that the user is likely to perform the set of movements.

19. A method comprising:
initializing a wearable stimulation array comprising:
a set of configurable electrodes each configured to contact a different portion of a surface of a body of a user when the wearable stimulation array is worn by the user;
a power source;
a memory storing a machine-learned movement model trained using measured movement data associated with respective actuation instructions, the movement model configured to determine actuation instructions likely to stimulate a set of movements, each actuation instruction specifying an electrical signal to be transmitted from a given electrode to a different electrode; and
a controller coupled to the set of configurable electrodes, the memory, and the power source;
stimulating a first movement of the set of movements by configuring current from the power source to flow in a direction between a first electrode and a first set of electrodes such that the first electrode is configured to operate as an anode; and
stimulating a second movement of the set of movements by configuring the current to flow in a different direction between the first electrode and a second set of electrodes such that the first electrode is configured to operate as a cathode.

20. A non-transitory computer readable storage medium storing executable instructions that, when executed by one or more processors, cause the one or more processors to perform steps comprising:
initializing a wearable stimulation array comprising:
a set of configurable electrodes each configured to contact a different portion of a surface of a body of a user when the wearable stimulation array is worn by the user;
a power source;
a memory storing a machine-learned movement model trained using measured movement data associated with respective actuation instructions, the movement model configured to determine actuation instructions likely to stimulate a set of movements, each actuation instruction specifying an electrical signal to be transmitted from a given electrode to a different electrode; and
a controller coupled to the set of configurable electrodes, the memory, and the power source;
stimulating a first movement of the set of movements by configuring current from the power source to flow in a direction between a first electrode and a first set of electrodes such that the first electrode is configured to operate as an anode; and
stimulating a second movement of the set of movements by configuring the current to flow in a different direction between the first electrode and a second set of electrodes such that the first electrode is configured to operate as a cathode.

* * * * *